United States Patent
Park et al.

(10) Patent No.: US 12,141,694 B2
(45) Date of Patent: Nov. 12, 2024

(54) ABDOMINAL MULTI-ORGAN SEGMENTATION WITH ORGAN-ATTENTION NETWORKS

(71) Applicant: The Johns Hopkins University, Baltimore, MD (US)

(72) Inventors: Seyoun Park, Baltimore, MD (US); Alan Yuille, Baltimore, MD (US); Elliott Fishman, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 353 days.

(21) Appl. No.: 17/605,847

(22) PCT Filed: Apr. 23, 2020

(86) PCT No.: PCT/US2020/029631
§ 371 (c)(1),
(2) Date: Oct. 22, 2021

(87) PCT Pub. No.: WO2020/219757
PCT Pub. Date: Oct. 29, 2020

(65) Prior Publication Data
US 2022/0215646 A1    Jul. 7, 2022

Related U.S. Application Data

(60) Provisional application No. 62/837,679, filed on Apr. 23, 2019.

(51) Int. Cl.
*G06N 3/08*        (2023.01)
*G06V 10/82*       (2022.01)
(Continued)

(52) U.S. Cl.
CPC ............... *G06N 3/08* (2013.01); *G06V 10/82* (2022.01); *G16H 30/40* (2018.01); *G16H 50/20* (2018.01)

(58) Field of Classification Search
CPC .......... G06N 3/08; G06N 3/045; G06V 10/82; G06V 2201/031; G16H 30/40;
(Continued)

(56) References Cited

U.S. PATENT DOCUMENTS 9,739,783 B1 *  8/2017  Kumar ............. G01N 33/57449
9,811,906 B1 * 11/2017  Vizitiu .................. G06T 7/0012
(Continued)

FOREIGN PATENT DOCUMENTS

CN    109685809      4/2019
EP      3252671      5/2016
(Continued)

OTHER PUBLICATIONS

Abraham et al., "Extracting Brain Regions from Rest fMRI with Total-Variation Constrained Dictionary Learning," MICCAI., 2013, 16:2:607-15.
(Continued)

*Primary Examiner* — Mahendra R Patel
(74) *Attorney, Agent, or Firm* — Fish & Richardson P.C.

(57) ABSTRACT

Systems, methods, and apparatus for segmenting internal structures depicted in an image. In one aspect, a method includes receiving data representing image data that depicts internal structures of a subject, providing an input data structure to a machine learning model, wherein the input data structure comprises fields structuring data that represents the received data representing the image data that depicts internal structures of the subject, wherein the machine learning model is a multi-stage deep convolutional network that has been trained to segment internal structures depicted by one or more images, receiving output data generated by the machine learning model based on the machine learning model's processing of the input data structure, and processing the output data to generate render-
(Continued)

ing data that, when rendered, a computer, causes the computer to output, for display, data that visually distinguishes between different internal structures depicted by the image data.

18 Claims, 6 Drawing Sheets

(51) Int. Cl.
G16H 30/40 (2018.01)
G16H 50/20 (2018.01)
(58) Field of Classification Search
CPC ............... G16H 50/20; G06F 18/2413; G06T 2207/10081; G06T 2207/20081; G06T 2207/30004; G06T 7/11; G06T 2207/20084; A61B 6/463; A61B 6/03; A61B 6/5217
USPC ........................................................ 382/131
See application file for complete search history.

(56) References Cited

U.S. PATENT DOCUMENTS

| | | | |
|---|---|---|---|
| 9,947,102 B2 | 4/2018 | Xu et al. | |
| 9,965,863 B2* | 5/2018 | Xu | G06N 3/084 |
| 10,140,544 B1 | 11/2018 | Zhao et al. | |
| 11,049,250 B2* | 6/2021 | Nye | G06N 5/046 |
| 11,308,623 B2 | 4/2022 | Yuille et al. | |
| 2010/0067754 A1* | 3/2010 | Collins | G06F 18/254 |
| | | | 382/128 |
| 2012/0230572 A1* | 9/2012 | Kohlberger | G06V 10/7553 |
| | | | 382/131 |
| 2015/0003703 A1* | 1/2015 | Franz | A61B 6/481 |
| | | | 382/128 |
| 2016/0098833 A1 | 4/2016 | Tsadok et al. | |
| 2017/0249744 A1* | 8/2017 | Wang | G06T 1/60 |
| 2018/0042565 A1 | 2/2018 | Wilson et al. | |
| 2018/0108124 A1* | 4/2018 | Guo | G06V 30/18057 |
| 2019/0105009 A1* | 4/2019 | Siemionow | A61B 6/5229 |
| 2019/0220975 A1* | 7/2019 | Hsieh | G06N 3/08 |
| 2019/0258878 A1 | 8/2019 | Koivisto et al. | |
| 2020/0202507 A1* | 6/2020 | Ceccaldi | G06N 3/006 |
| 2020/0245960 A1 | 8/2020 | Richter et al. | |
| 2020/0278681 A1 | 9/2020 | Gier et al. | |
| 2020/0342600 A1* | 10/2020 | Sjöstrand | A61B 6/032 |
| 2020/0356899 A1 | 11/2020 | Rejeb Sfar et al. | |
| 2020/0372626 A1 | 11/2020 | Dal Mutto et al. | |
| 2021/0012505 A1 | 1/2021 | Yuille et al. | |
| 2022/0392641 A1 | 12/2022 | Yuille et al. | |

FOREIGN PATENT DOCUMENTS

| | | | | |
|---|---|---|---|---|
| EP | 3392832 A1 * | 10/2018 | ........... | G06K 9/2054 |
| WO | WO 2016182551 | 11/2016 | | |
| WO | WO 2017210690 | 12/2017 | | |
| WO | WO 2018015080 | 1/2018 | | |
| WO | WO 2018015414 | 1/2018 | | |
| WO | WO 2019005722 | 1/2019 | | |
| WO | WO-2019005722 A1 * | 1/2019 | ......... | G06F 18/2413 |

OTHER PUBLICATIONS

Ansari et al. "Role of Magnetic Resonance Imaging in the Detection and Characterization of Solid Pancreatic Nodules: An Update." World Journal of Radiology, 28, 7(11), Nov. 2015, 361-374.
Asman et al., "Formulating spatially varying performance in the statistical fusion framework," IEEE Trans. On Med, Imaging, 2012, 31:6:1326-1336.
Asman et al., "Non-local statistical label fusion for multi-atlas segmentation," Med. Image Anal., Feb. 2013, 17:2:194-208.
Aydogan et al., "Analysis of Trabecular Bone Microstructure Using Contour Tree Connectivity, " MICCAI., 2013, 16:2:428-35.
Bieth et al., "Atlas Construction for Dynamic (4D) PET Using Diffeomorphic Transformations," MICCAI, 2013, 35-42.
Boykov et al, "Fast approximate energy minimization via graph cuts," IEEE Transactions on PAMI, 2001, 23:11:122-1239.
Brosch et al., "Manifold Learning of Brain MRIs by Deep Learning," MICCAI., 2013, 16:2:633-40.
Cerrolaza et al., "Multiresolution Hierarchical Shape Models in 3D Subcortical Brain Structures," MICCAI., 2013, 16:2:641-8.
Chang et al., "Characterization of Tissue Histopathology via Predictive Sparse Decomposition and Spatial Pyramid Matching," MICCAI, 2013, 8150:91-98.
Chatelain et al., "Learning from Multiple Experts with Random Forests: Application to the Segmentation of the Midbrain in 3D Ultrasound," MICCAI, 2013, 16:2:230-7.
Chen et al., "Attention to scale: Scale-aware semantic image segmentation," In proceedings of the IEEE conf. on CCVPR, 2016, 3640-3649.
Chen et al., "DeepLab: Semantic Image Segmentation with Deep Convolutional Nets, Atrous Convolution, and Fully Connected CRFs", IEEE Transactions on Pattern Analysis and Machine Intelligence, 2016, 40(4): 834-848.
Chen et al., "VoxResNet:Deep voxelwise residual networks for brain segmentation from 3D MR images," NeuroImage, 2018, 170:446-455.
Chu et al., "Multi-organ segmentation based on spatially-divided probabilistic atlas from 3D abdominal CT images," Lecture Notes in Comp. Sci., 2013, 8150LNCS(part 2) 165-172.
Ciompi et al., "Stent Shape Estimation through a Comprehensive Interpretation of Intravascular Ultrasound Images," MICCAI, 2013, 16:2:345-52.
Ciresan et al., "Mitosis Detection in Breast Cancer Histology Images with Deep Neural Networks," MICCAI., 2013, 16:2:411-8.
Cisek et al., "3D U-Net: Learning dense volumetric segmentation from sparse annotation," MICCAI, 2016, 424-432.
Cruz-Roa et al., "A Deep Learning Architecture for Image Representation, Visual Interpretability and Automated Basal-Cell Carcinoma Cancer Detection," MICCAI., 2013, 16:2:403-10.
Da Mota et al., "Enhancing the Reproducibility of Group Analysis with Randomized Brain Parcellations," MICCAI., 2013, 16:2:591-8.
Datar et al., "Geodesic Distances to Landmarks for Dense Correspondence on Ensembles of Complex Shapes," MICCAI., 2013, 16:19-26.
De Silva et al., "Improving 2D-3D Registration Optimization Using Learned Prostate Motion Data," MICCAI, 2013, 16:2:124-31.
Dinse et al., "A Histology-Based Model of Quantitative T1 Contrast for In-vivo Cortical Parcellation of High-Resolution 7 Tesla Brain MR Images,".
Dou et al., "3D deeply supervised network for automatic liver segmentation from CT volumes," Med. Image Analysis, Oct. 2017, 41:40-54.
Dou et al., "Multilevel Contextual 3-D CNNs for False Positive Reduction in Pulmonary Nodule Detection", IEEE TBE, 2017, 64(7): 1558-1567.
Durichen et al., "Respiratory Motion Compensation with Relevance Vector Machines," MICCAI., 2013, 108-115.
Everingham et al., The PASCAL visual object classes challenge 2012 (VOC2012) results. 2012, Pascal2, 24 pages.
Farag et al., "Automatic pancreas segmentation using coarse to-fine superpixel labeling," Deep learning ans Convutional Neural Networks for Medical Computing, 2017.
Forman et al., "Free-Breathing Whole-Heart Coronary MRA: Motion Compensation Integrated into 3D Cartesian Compressed Sensing Reconstruction," MICCAI., 2013, 16:2:575-82.
Gao et al., "Incremental Learning with Selective Memory (ILSM): Towards Fast Prostate Localization for Image Guided Radiotherapy," MICCAI., 2013, 16:2:378-386.
Gibson et al., "Automatic multi-organ segmentation on abdominal CT with dense V-networks," IEEE Trans. Med. Imaging, Aug. 2018, 37:8:1822-1834.

(56) References Cited

OTHER PUBLICATIONS

Ginsburg et al., "Variable Importance in Nonlinear Kernels (VINK): Classification of Digitized Histopathology," MICCAI., 2013, 16:2:238-45.

Glocker et al., "Vertebrae Localization in Pathological Spine CT via Dense Classification from Sparse Annotations," MICCAI., 2013, 16:2:262-70.

Gomez et al., "3D Intraventricular Flow Mapping from Colour Doppler Images and Wall Motion," MICCAI,2013, 16:2:476-83.

Grbic et al., "Image-Based Computational Models for TAVI Planning: From CT Images to Implant Deployment," MICCAI., 2013, 16:2:395-402.

Hacihaliloglu eet al., "Statistical Shape Model to 3D Ultrasound Registration for Spine Interventions Using Enhanced Local Phase Features," MICCAI., 2013, 16:2:361-8.

Hamy et al., "Respiratory Motion Correction in Dynamic-MRI: Application to Small Bowel Motility Quantification during Free Breathing, " MICCAI, 2013, 16:2:132-40.

Havaei et al.,"Brain tumor segmenation with deep neural networks," Medical Image analysis, Jan. 2017, 35:18-31.

He et al., "Deep Residual Learning for Image Recognition", 2016, CVPR, 770-778.

Heimann et al., "Comparison and evaluation of methods for live segmentation from CT datasets," IEEE Transactions on Medical Imaging, Aug. 2009, 28:8:1251-1265.

Hibar er al., "Genetic Clustering on the Hippocampal Surface for Genome-Wide Association Studies," MICCAI., 2013, 16:2:690-7.

Hu et al., "Automated Separation of Binary Overlapping Trees in Low-Contrast Color Retinal Images," MICCAI., 2013, 16:2:436-43.

Huang et al., "A New Sparse Simplex Model for Brain Anatomical and Genetic Network Analysis," MICCAI., 2013, 16:2:625-632.

Huh et al., "Apoptosis Detection for Non-adherent Cells in Time-lapse Phase Contrast Microscopy," MICCAI, 2013, 8150: 59-66.

Hussein et al., "Lung and Pancreatic Tumor Characterization in the Deep Learning Era: Novel Supervised and Unsupervised Learning Approaches", IEEE Transactions on Medical Imaging, 2019, 38(8): 1777-1787,.

Hussein et al., "Supervised and unsupervised tumor characterization in the deep learning era," ArXiv, 2018.

Iglesias et al., Multi-atlas segmentation of biomedical images: A survey, Med Image Anal., Aug. 2015, 24:1:205-219.

Imani et al., "Ultrasound-Based Characterization of Prostate Cancer: An in vivo Clinical Feasibility Study," MICAAI, 2013, 16:2:279-86.

International Preliminary Report on Patentability in Appl. No. PCT/US2020/029631, dated Sep. 28, 2021, 6 pages.

International Search Report in Appl. No. PCT/US2020029631, dated Jul. 30, 2020, 6 pages.

Jiang et al., "Predictive Models of Resting State Networks for Assessment of Altered Functional Connectivity in MCI," MICCAI, 2013, 16:2:674-81.

Jimenez del Toro et al., "Epileptogenic Lesion Quantification in MRI Using Contralateral 3D Texture Comparisons," MICCAI., 2013, 16:2:353-60.

Kamnitsas et al., "Effcient multi-scale 3D CNN with fully connected CRF for accurate brain lesion segmentation," Med. Image Analysis, Feb. 2017, 36:61-78.

Karasawa e al., "Multi-atlas pancreas segmentation: Atlas selection based on vessel structure," Med. Image Analysis, 2017, 39:18-28.

Kirbas et al., "A review of vessel extraction techniques and algorithms," ACM Computing Surveys, 2004, 36:2:81-121.

Koenig et al., "The Spatial Periodicity of Grid Cells Is Not Sustained During Reduced Theta Oscillations," Science, 2011, 332:592-595.

Kong et al., "RON: Reverse connection with objectness prior networks for object detection," IEEE Conference on Computer Vision Pattern Recognition, Jul. 2017, 5936-5944.

Kortylewski et al., "Compositional Convolutional Neural Networks: A Deep Architecture with Innate Robustness to Partial Occlusion," arXiv:2003.04490v3, Apr. 2020, 10 pages.

Krizkevsky et al., "ImageNet Classification with Deep Convolutional Neural Networks", NIPS, 9 pages, 2012.

Kroeger et al., "Learning to Segment Neurons with Non-local Quality Measures," MICCAI., 2013, 16:2:419-27.

Kronman et al., "Image Segmentation Errors Correction by Mesh Segmentation and Deformation," MICCAI., 2013, 206-213.

Kwitt et al., "Studying Cerebral Vasculature Using Structure Proximity and Graph Kernels," MICCAI., 2013, 16:2:534-541.

Lesage et al., "A review of 3D vessel lumen segmentation techniques: Models, features and extraction schemes," SciDirect., 2009, 13:819-845.

Li et al., "Automatic liver segmentation based shape constraints and deformable graph cut in CT images," IEEE tans. On Image Proc., Dec. 2015, 24:12.

Liao et al., "Representation Learning: A Unified Deep Learning Framework for Automatic Prostate MR Segmentation," MICCAI., 2013, 16:2:254-61.

Lindner et al., "Accurate Bone Segmentation in 2D Radiographs Using Fully Automatic Shape Model Matching Based On Regression-Voting," MICCAI., 2013, 181-189.

Liu et al., "Automatic pancreas segmentation via coarse location and ensemble learning," IEEE Access, 2019, 9 pages.

Liu et al., "High-Order Graph Matching Based Feature Selection for Alzheimer's Disease Identification," MICCAI, 2013, 16:2:311-318.

Liu et al., "A Variational Framework for Joint Detection and Segmentation of Ovarian Cancer Metastases," MICCAI., 2013, 8150:83-90.

Liu et al., "Joint shape representation and classification for detecting PDAC," MLMI@MICCAI, 2019.

Liu et al., "Longitudinal Modeling of Glaucoma Progression Using 2-Dimensional Continuous-Time Hidden Markov Model," MICCAI., 2013, 16:2:444-451.

Liu et al., "Multifold Bayesian Kernelization in Alzheimer's Diagnosis," MICCAI., 2013, 16:2:303-10.

Liu et al., "Tracking of Carotid Arteries in Ultrasound Images," MICCAI., 2013, 16:2:526-33.

Lombaert et al., "Joint Statistics on Cardiac Shape and Fiber Architecture," MICCAI., 2013, 16:2:492-500.

Long et al., "Fully Convolutional Networks for Semantic Segmentation," CVPR, 2015, 3431-3440.

Lorenzi et al., "Sparse Scale-Space Decomposition of Volume Changes in Deformations Fields," MICCAI., 2013, 16:2:328-35.

Lorza et al., "Carotid Artery Lumen Segmentation in 3D Free-Hand Ultrasound Images Using Surface Graph Cuts," MICCAI., 2013, 16:2: 542-9.

Lugo-fagundo et al., "Deep learning in radiology: Now the real work begins," J. Am. Coll. Radiol., Feb. 2018, 15:2:364-367.

Lundervold et al., "An overview of deep learning in medical imaging focusing on MRI," Zeitschrift für Medizinische Physik, May 2019, 29:2:102-127.

Lv et al., "Group-Wise FMRI Activation Detection on Corresponding Cortical Landmarks," MICCAI., 2013, 16:2:665-73.

Lv et al., "Modeling Dynamic Functional Information Flows on Large-Scale Brain Networks," MICCAI., 2013, 698-705.

Mahapatra et al., "Semi-Supervised and Active Learning for Automatic Segmentation of Crohn's Disease," MICCAI., 2013, 16:2:214-21.

Mahrooghy et al., "Heterogeneity Wavelet Kinetics from DCE-MRI for Classifying Gene Expression Based Breast Cancer Recurrence Risk," MICCA., 2013, 16:2:295-302.

Maier et al., "A gentle introduction to deep learning in medical imaging processing," J. of Med. Physics, Dec. 2018.

Marreiros et al., "Non-rigid Deformation Pipeline for Compensation of Superficial Brain Shift," MICCAI., 2013, 16:2:141-8.

McLeod et al., "Spatio-temporal Dimension Reduction of Cardiac Motion for Group-Wise Analysis and Statistical Testing," MICCAI., 2013, 16:2:501-8.

Melbourne et al., "Measurement of Myelin in the Preterm Brain: Multi-compartment Diffusion Imaging and Multi-component T2 Relaxometry," MICCAI., 2013, 16:2:336-44.

Mharib et al., "Survey on liver CT image segmentation methods," Artif Intell rev., 2012, 37:83-95.

(56) References Cited

OTHER PUBLICATIONS

Milletari et al., "V-Net: Fully Convolutional Neural Networks for Volumetric Medical Image Segmentation", 2016 Fourth International Conference on 3D Vision,2016, 565-571.
Mori et al., Medical Image computing and computer-assisted intervention-MICCAI 2013, 16th Int. Conf., Sep. 2013, 36 pages.
Nascimento et al., Multi-atlas segmentation using manifold learning with deep belief neworks, IEE, 2016, 4 pages.
NCBI.gov [online], "Pancreatic cancer treatment (adult) (PDQ)," May 15, 2020, retrieved on Oct. 5, 2020, retrieved from URL<https://www.ncbi.nlm.nih.gov/books/NBK65957/?report-printable. 37 pages.
Nouranian et al., "An Automatic Multi-atlas Segmentation of the Prostate in Transrectal Ultrasound Images Using Pairwise Atlas Shape Similarity," MICCAI, 2013, 16:2:173-80.
Okada et al., "Abdominal multi-organ segmentation from CT images using conditional shape-location and unsupervised intensity priors," Med. Image Anal., Dec. 2015, 26:1:1-18.
Oktay et al., "Biomechanically driven registration of pre- to intraoperative 3D images for laparoscopic surgery," MICCAI., 2013, 16:2:1-9.
Ospina et al., "A Tensor-Based Population Value Decomposition to Explain Rectal Toxicity after Prostate Cancer Radiotherapy," MICCAI., 2013, 16:2:387-94.
PCT International Preliminary Report on Patentability in International Application No. PCT/US2020/060061, mailed on May 27, 2022, 9 pages.
PCT International Search Report and Written Opinion in International Application No. PCT/US2020/060061, mailed on Mar. 1, 2021, 14 pages.
Petersen et al., "Quantitative Airway Analysis in Longitudinal Studies Using Groupwise Registration and 4D Optimal Surfaces," MICCAI., 2013, 16:2:287-94.
Piuze et al., "Cardiac Fiber Inpainting Using Cartan Forms," MICCAI, 2013, 16:2:509-17.
Porras et al., "Myocardial Motion Estimation Combining Tissue Doppler and B-mode Echocardiographic Images," MICCAI., 2013, 16:2:484-91.
Prasoon et al., "Deep Feature Learning for Knee Cartilage Segmentation Using a Triplanar Convolutional Neural Network," MICCAI., 2013, 16:2:246-53.
Prevost et al., "Registration of Free-Breathing 3D+t Abdominal Perfusion CT Images via Co-segmentation," MICCAI., 2013, 16:2:99-107.
Qiu et al., "Fast Globally Optimal Segmentation of 3D Prostate MRI with Axial Symmetry Prior," MICCAI., 2013, 16:2:198-205.
Rafii-Tari et al., "Learning-Based Modeling of Endovascular Navigation for Collaborative Robotic Catheterization," MICCAI., 2013, 16:2:369-77.
Rajchl et al., "Deepcut: Object segmentation from bounding box annotations using convulutional neural networks," IEE Trans. Med. Imaging., 2016, 10 pages.
Romain et al., "A Multi-task Learning Approach for Compartmental Model Parameter Estimation in DCE-CT Sequences,"MICAA., 2013, 16:2:271-8.
Ronneberger et al., "U-Net: Convolutional Networks for Biomedical Image Segmentation", MICCAR, 234-241, 2015.
Roth et al., "Deep convolutional networks for pancreas segmentation in CT imaging," SPIE Med., Imaging, 2015, 9413-94131G.
Roth et al., "DeepOrgan: Multi-level Deep Convolutional Networks for Automated Pancreas Segmentation", MICCAI, 556-564, 2015.
Roth et al., "Hierarchical 3D fully convolutional networks for multi-organ segmentation," arXiv., Apr. 2017, arXiv: 1704.06382:11 pages.
Roth et al., Spatial aggregation of holistically-nested convolutional neural networks for automated pancreas localization and segmentation, Medical Image Analysis, Apr. 2018, 45:94-107.
Roth et al., "Spatial Aggregation of Holistically-Nested Networks for Automated Pancreas Segmentation", 2016, MICCAI, 451-459.
Roth et al., "Towards dense volumetric pancreas segmentation in CT using 3D fully conventional networks," Medical Imaging, 2018, 6 pages.
Sabuncu et al., "A generative model for image segmentation based on label fusion," IEE Trans. On Med. Imaging, Oct. 2010, 29:10:1714-1729.
Saito et al., "Joint optimization of segmentation and shape prior from level-set-based statistical shape model, and its application to the automated segmentation of abdominal organs," Med. Image Analysis, 2016, 28:46-65.
Seito et al., "Pulmonary nodule detection in CT images: False positive reduction using multi-view convolutional networks," IEE Trans. On Med. Imag., May 2016, 35:5:1160-1169.
Shen et al., "A Spatial Mixture Approach to Inferring Sub-ROI Spatio-temporal Patterns from Rapid Event-Related fMRI Data," MICCAI., 2013, 16:2:657-64.
Shen et al., Deep learning in medical image analysis, Annu rev. Biomed. En., 2017, 19:221-248.
Simpson et al., "A bayesian approach for spatially adaptive regularisation in Non-rigid registration," MICCAI., 2013, 10-18.
Song et al., "Discriminative Data Transform for Image Feature Extraction and Classification," MICCAI., 2013, 16:2:452-9.
Suk et al., "Deep Learning-Based Feature Representation for AD/MCI Classification," MICCAI., 2013, 16:2:583-90.
Tang et al., "Random Walks with Efficient Search and Contextually Adapted Image Similarity for Deformable Registration," MICCAI, 2013, 43-50.
Tong et al., "Multiple Instance Learning for Classification of Dementia in Brain MRI," Med. Image Anal., Jul. 2014, 18:5:808-18.
Uzunbas et al., "Collaborative Multi Organ Segmentation by Integrating Deformable and Graphical Models," MICCAI, 2013, 157-164.
Vincent et al., "Bayesian Joint Detection-Estimation of Cerebral Vasoreactivity from ASL fMRI Data," MICCAI, 2013, 616-624.
Wang et al., "Image quality assessment: Form error visibility to structural similarity," IEE. Trans. On Image. Proces., Apr. 2004, 13:4:600-612.
Wang et al., "Interactive Retinal Vessel Extraction by Integrating Vessel Tracing and Graph Search," MICCAI., 2013, 16:2:567-74.
Wang et al., "Automated Embryo Stage Classification in Time-Lapse Microscopy Video of Early Human Embryo Development," MICCAI., 2013, 16:2:460-7.
Wang et al., "Image Quality Assessment: From Error Visibility to Structural Similarity," IEEE Transactions on Image Processing, Apr. 2004, 13:4:600-612.
Wang et al., "Robust Object Detection under Occlusion with Context-Aware CompositionalNets," 2020 IEEE/CVF Conference on Computer Vision and Pattern Recognition (CVPR), Jun. 2020, pp. 12642-12651.
Wang et al., "Sequential Monte Carlo Tracking for Marginal Artery Segmentation on CT Angiography by Multiple Cue Fusion," MICCAI., 2013, 16:2:518-525.
Wang et al.,"Abdominal multi-organ segmentation with organ-attention networks and statistical fusion," Medical Image Analysis, 2019, 55:88-102.
Warfield et al., "Simultaneous truth and performance level estimation (STAPLE): An algorithm for the validation of image segmentation," IEE Trans. Med. Imaging., Jul. 2004, 23:7:903-921.
Wasza et al., "Real-Time Respiratory Motion Analysis Using Manifold Ray Casting of Volumetrically Fused Multi-view Range Imaging," MICCAI., 2013, 16:2:116-23.
Wee et al., "Identification of MCI Using Optimal Sparse MAR Modeled Effective Connectivity Networks," MICCAI., 2013, 16:2:319-327.
Wolz et al., "Automated abdominal multi-organ segmentation with subject-specific atlas generation," IEE Trans. On Med. Imaging, Sep. 2013, 32:9:1723-1730.
Wu et al., "Unsupervised Deep Feature Learning for Deformable Registration of MR Brain Images," MICCAI., 2013, 16:2:649-56.
Xia et al., "Bridging the Gap Between 2D and 3D Organ Segmentation with Volumetric Fusion Net", MICCAI, 445-453, 2018.

(56) References Cited

OTHER PUBLICATIONS

Xie et al., "Holistically-Nested Edge Detection", Proceedings of the IEEE International Conference on Computer Vision, 2015, 1395-1403.
Xu et al., "A Symmetric 4D Registration Algorithm for Respiratory Motion Modeling," MICCAI., 2013, 16:2:149-56.
Xu et al., "Automatic Grading of Nuclear Cataracts from Slit-Lamp Lens Images Using Group Sparsity Regression," MICCAI., 2013, 16:2:468-75.
Xu et al., "Spatially Constrained Random Walk Approach for Accurate Estimation of Airway Wall Surfaces," MICCAI., 2013, 16:2:559-566.
Ye et al., "Pathological Site Retargeting under Tissue Deformation Using Geometrical Association and Tracking," MICCAI., 2013, 16:2:67-74.
Yokota et al., "Automated CT Segmentation of Diseased Hip Using Hierarchical and Conditional Statistical Shape Models," MICCAI, 2013 190-197.
Yoldemir et al., "Overlapping Replicator Dynamics for Functional Subnetwork Identification," MICCAI., 2013, 16:2:682-9.
Yu et al., "Recurrent saliency transformation network: incorporating multi-stage visual cues for small organ segmentation," Arxiv, 2017.
Yuille et al., "Abdominal multi-organ segmentation with organ-attention networks and statistical fusion," Med., Image Anal., Jul. 2019, 55:88-102.
Zhang et al., "Large Deformation Diffeomorphic Registration of Diffusion-Weighted Images with Explicit Orientation Optimization."
Zhang et al., "Personalized Pancreatic Tumor Growth Prediction via Group Learning", MICCAI, 2017, 424-432.
Zhao et al., "Hierarchical Constrained Local Model Using ICA and Its Application to Down Syndrome Detection," MICCAI., 2013, 16:2:222-9.
Zheng et al., "Optic disc and cup segmentation from color fundus photograph using graph cut with priors," MICCAI., 2013, 16:75-82.
Zhou et al., "A Fixed-Point Model for Pancreas Segmentation in Abdominal CT Scans", MICCAI,2017, 693-701.
Zhou et al., "Deep Supervision for Pancreatic Cyst Segmentation in Abdominal CT Scans", MICCAI, 2017, 222-230.
Zhou et al., "Pancreas Segmentation in Abdominal CT Scan: A Coarse-to-Fine Approach." arXiv:1612.08230v1, Dec. 2016, pp. 1-13.
Zhu et al., "A 3D Coarse-to-Fine Framework for Volumetric Medical Image Segmentation", International Conference on 3D Vision, 682-690, 2018.
Zhu et al., "Deep Learning Representation using Autoencoder for 3D Shape Retrieval", Neurocomputing 204: 41-50, 2016.
Zhu et al., "Multi-scale coarse-to-fine segmentation for screening pancreatic ductal adenocarcinoma," ArXiv, 2019.
Zhu et al., "Random Walks with Adaptive Cylinder Flux Based Connectivity for Vessel Segmentation," MICCAI., 2013, 16:2:550-8.
Zhuang et al., Multi-scale patch and multi-modality atlases for whole heart segmentation of MRI, Med Image Analysis, 2016, 31:77-87.
Zu et al., "Robust multi-atlas propagation by deep sparse representation," Pattern Recognition, 2017, 63:511-517.
Extended Search Report in European Appln. No. 20794854.8, dated Apr. 19, 2023, 5 pages.
Hu et al. "Brain Tumor Segmentation Using Multi-Cascaded Convolutional Neural Networks and Conditional Random Field," IEEE Access, Jul. 8, 2019, 7:92615-92629.
Wang et al., "Abdominal Multi-organ Segmentation with Organ-Attention Networks and Statistical Fusion," CoRR, submitted on Apr. 23, 2018, arXiv:1804.08414v1, 21 pages.
Wang et al., English translation of CN 109685809 A, published on Apr. 26, 2019, 14 pages.
Arthur et al., "k-means++: The advantages of careful seeding," Proceedings of the Eighteenth Annual ACM-SIAM Symposium on Discrete Algorithms, Jan. 2007, 1027-1035.
Banerjee et al., "Clustering on the unit hypersphere using von mises-fisher distributions," Journal of Machine Learning Research, Sep. 2005, 6:1345-1382.
Bienenstock et al., "Compositionality, MDL Priors, and Object Recognition," Proceedings of the 9th International Conference on Neural Information Processing Systems, Dec. 1996, 838-844.
Cai et al., "Cascade R-CNN: Delving into High Quality Object Detection," Proceedings of the IEEE/CVF Conference on Computer Vision and Pattern Recognition (CVPR), Jun. 2018, 6154-6162.
Carlson et al., "A Sparse Object Coding Scheme in Area V4," Current Biology, Feb. 22, 2011, 21(4):288-293.
Dai et al., "Unsupervised learning of dictionaries of hierarchical compositional models," Proceedings of the IEEE Conference on Computer Vision and Pattern Recognition, Jun. 2014, 2505-2512.
Deng et al., "ImageNet: A Large-Scale Hierarchical Image Database," Proceedings of the IEEE Conference on Computer Vision and Pattern Recognition, Jun. 2009, 248-255.
DeVries et al., "Improved regularization of convolutional neural networks with cutout," CoRR, submitted on Nov. 29, 2017, arXiv:1708.04552v2, 8 pages.
Fawzi et al., "Measuring the effect of nuisance variables on classifiers," Proceedings of the British Machine Vision Conference (BMVC), Sep. 2016, 12 pages.
Fidler et al., "Learning a hierarchical compositional shape vocabulary for multiclass object representation," CoRR, submitted on Aug. 23, 2014, arXiv:1408.5516v1, 17 pages.
Fodor et al., "Connectionism and cognitive architecture: A critical analysis," Cognition, Mar. 1988, 28(1-2):3-71.
George et al., "A generative vision model that trains with high data efficiency and breaks text-based captchas," Science, Oct. 26, 2017, 358(6368):eaag2612, 19 pages.
Girshick et al., "Rich feature hierarchies for accurate object detection and semantic segmentation," Proceedings of the IEEE Conference on Computer Vision and Pattern Recognition (CVPR), Jun. 2014, 580-587.
Girshick, "Fast R-CNN," Proceedings of the IEEE International Conference on Computer Vision (ICCV), Dec. 2015, 1440-1448.
International Preliminary Report on Patentability in International Appln. No. PCT/US2022/033438, mailed on Dec. 28, 2023, 9 pages.
International Search Report and Written Opinion in International Appln. No. PCT/US2022/033438, mailed on Oct. 20, 2022, 10 pages.
Jin et al., "Context and hierarchy in a probabilistic image model," Proceedings of the 2006 IEEE Computer Society Conference on Computer Vision and Pattern Recognition (CVPR'06), Jun. 2006, 2145-2152.
Kingma et al., "Adam: A method for stochastic optimization," CoRR, submitted on Dec. 22, 2014, arXiv:1412.6980v1, 9 pages.
Kortylewski et al., "Compositional Convolutional Networks For Robust Object Classification under Occlusion," CoRR, submitted on May 29, 2019, arXiv:1905.11826v2, 12 pages.
Kortylewski et al., "Greedy structure learning of hierarchical compositional models," CoRR, submitted on Jan. 22, 2017, arXiv:1701.06171v1, 16 pages.
Kortylewski et al., "Probabilistic compositional active basis models for robust pattern recognition," Proceedings of the British Machine Vision Conference (BMVC), Sep. 2016, 12 pages.
Kortylewski, "Model-based image analysis for forensic shoe print recognition," Dissertation for the Degree of Doctor of Philosophy, University of Basel, Jun. 2017, 124 pages.
Lampert et al., "Beyond sliding windows: Object localization by efficient subwindow search," IEEE Conference on Computer Vision and Pattern Recognition (CVPR), Jun. 2008, 8 pages.
Li et al., "AOGNets: Compositional Grammatical Architectures for Deep Learning," Proceedings of the IEEE/CVF Conference on Computer Vision and Pattern Recognition (CVPR), Jun. 2019, 6220-6230.
Li et al., "SymmNet: A Symmetric Convolutional Neural Network for Occlusion Detection," Proceedings of the British Machine Vision Conference (BMVC), Sep. 2018, 14 pages.

(56) References Cited

OTHER PUBLICATIONS

Liao et al., "Learning deep parsimonious representations," Advances in Neural Information Processing Systems, Dec. 2016, 29:5076-5084.

Lin et al., "Microsoft COCO: Common Objects in Context," Computer Vision—ECCV 2014 (LNCS), Sep. 2014, 8693:740-755.

Reddy et al., "Occlusion-Net: 2D/3D Occluded Keypoint Localization Using Graph Networks," Proceedings of the IEEE/CVF Conference on Computer Vision and Pattern Recognition (CVPR), Jun. 2019, 7326-7335.

Ren et al., "Faster R-CNN: Towards Real-Time Object Detection with Region Proposal Networks," Advances in Neural Information Processing Systems, Dec. 2015, vol. 28, 9 pages.

Roe et al., "Toward a Unified Theory of Visual Area V4," Neuron, Apr. 12, 2012, 74(1):12-29.

Sasikumar et al., "First-pass processing of value cues in the ventral visual pathway," Current Biology, Feb. 8, 2018, 28(4):538-548.

Simonyan et al., "Very deep convolutional networks for large-scale image recognition," CoRR, submitted on Dec. 23, 2014, arXiv:1409.1556v5, 13 pages.

Stone et al., "Teaching Compositionality to CNNs," Proceedings of the IEEE/CVF Conference on Computer Vision and Pattern Recognition (CVPR), Jul. 2017, 5058-5067.

Sun et al., "Symmetric stereo matching for occlusion handling," Proceedings of the IEEE Computer Society Conference on Computer Vision and Pattern Recognition (CVPR), Jun. 2005, 399-406.

Tabernik et al., "Towards deep compositional networks," Proceedings of the 23rd International Conference on Pattern Recognition (ICPR), Dec. 2016, 3470-3475.

Tang et al., "Deeply Learned Compositional Models for Human Pose Estimation," Computer Vision—ECCV 2018 (LNCS), Sep. 2018, 11207:190-206.

Tang et al., "Towards a unified compositional model for visual pattern modeling," Proceedings of the IEEE International Conference on Computer Vision (ICCV), Oct. 2017, 2784-2793.

The Handbook of Brain Theory and Neural Networks, 2nd ed., Arbib (ed.), 2003, pp. 244-248.

Vaziri et al., "A channel for 3d environmental shape in anterior inferotemporal cortex," Neuron, Oct. 2014, 84(1):55-62.

Wang et al., "Detecting semantic parts on partially occluded objects," Proceedings of the British Machine Vision Conference (BMVC), Sep. 2017, 13 pages.

Wang et al., "Discovering Internal Representations from Object-CNNs Using Population Encoding," CoRR, submitted on Nov. 21, 2015, arXiv:1511.06855v1, 12 pages.

Wang et al., "Visual concepts and compositional voting," CoRR, submitted on Nov. 13, 2017, arXiv:1711.04451v1, 37 pages.

Xiang et al., "Beyond Pascal: A benchmark for 3D object detection in the wild," IEEE Winter Conference on Applications of Computer Vision, Mar. 2014, 75-82.

Xiang et al., "Object Detection by 3D Aspectlets and Occlusion Reasoning," IEEE International Conference on Computer Vision Workshops, Dec. 2013, 530-537.

Xiao et al., "Tdapnet: Prototype network with recurrent top-down attention for robust object classification under partial occlusion," CoRR, submitted on Sep. 9, 2019, arXiv:1909.03879v1, 11 pages.

Yamane et al., "A neural code for three-dimensional object shape in macaque inferotemporal cortex," Nature Neuroscience, Oct. 5, 2008, 11(11):1352-1360.

Yan et al., "Inferring occluded features for fast object detection," Signal Processing, May 2015, 110:188-198.

Yun et al., "CutMix: Regularization Strategy to Train Strong Classifiers with Localizable Features," CoRR, submitted on May 13, 2019, arXiv:1905.04899v1, 14 pages.

Zhang et al., "Deepvoting: A robust and explainable deep network for semantic part detection under partial occlusion," Proceedings of the IEEE/CVF Conference on Computer Vision and Pattern Recognition (CVPR), Jun. 2018, 1372-1380.

Zhang et al., "Interpretable convolutional neural networks," Proceedings of the IEEE/CVF Conference on Computer Vision and Pattern Recognition (CVPR), Jun. 2018, 8827-8836.

Zhang et al., "Occlusion-aware R-CNN: Detecting Pedestrians in a Crowd," CoRR, submitted on Jul. 23, 2018, arXiv:1807.08407v1, 17 pages.

Zhu et al., "Robustness of Object Recognition under Extreme Occlusion in Humans and Computational Models," Proceedings of the 41st Annual Meeting of the Cognitive Science Society: Creativity + Cognition + Computation, Jul. 2019, 7 pages.

Zhu et al., "Unsupervised Structure Learning: Hierarchical Recursive Composition, Suspicious Coincidence and Competitive Exclusion," Computer Vision—ECCV 2008 (LNCS), Oct. 2008, 5303:759-773.

* cited by examiner

200

```
OBTAIN AN INTERNAL IMAGE OF AN
ABDOMEN OF A SUBJECT                         210
```

↓

```
PROVIDE THE OBTAINED INTERNAL IMAGE AS AN INPUT
TO A FIRST STAGE OF A MACHINE LEARNING MODEL
THAT IS TRAINED TO GENERATE A FIRST PROBABILITY
MAP THAT INCLUDES, FOR EACH PIXEL, DATA
INDICATING A LIKELIHOOD THAT THE PIXEL
CORRESPONDS TO A PARTICULAR ORGAN BASED ON
PROCESSING OF THE OBTAINED INTERNAL IMAGE   220
```

↓

```
GENERATE INPUT DATA FOR A SECOND STAGE OF A
MACHINE LEARNING MODEL BASED ON (I) THE
OBTAINED INTERNAL IMAGE AND (II) THE FIRST
PROBABILITY MAP                              230
```

↓

```
PROVIDE THE GENERATED INPUT DATA TO A SECOND
STAGE OF A MACHINE LEARNING MODEL THAT IS
TRAINED TO GENERATE A SECOND PROBABILITY MAP
THAT INCLUDES, FOR EACH PIXEL, DATA INDICATING A
LIKELIHOOD THAT THE PIXEL CORRESPONDS TO A
PARTICULAR ORGAN BASED ON THE PROCESSING OF
THE INPUT GENERATED AT STAGE (230)           240
```

↓

```
GENERATE, BASED ON THE SECOND PROBABILITY MAP
GENERATED BY THE SECOND MACHINE LEARNING
MODEL, OUTPUT IMAGE DATA, THE OUTPUT IMAGE
DATA, WHEN RENDERED BY A USER DEVICE, CAUSES
THE USER DEVICE TO DISPLAY A GRAPHICAL
REPRESENTATION OF THE OBTAINED INTERNAL IMAGE
THAT VISUALLY DISTINGUISHES BETWEEN DIFFERENT
ORGANS IN THE INTERNAL IMAGE                 250
```

FIG. 2

ABDOMINAL MULTI-ORGAN SEGMENTATION WITH ORGAN-ATTENTION NETWORKS

CROSS-REFERENCE TO RELATED APPLICATION

This application is a National Stage application under 35 U.S.C. § 371 of International Application No. PCT/US2020/029631 having an International Filing Date of Apr. 23, 2020, which claims the benefit of U.S. Provisional Patent Application No. 62/837,679 filed Apr. 23, 2019, the entirety of which are incorporated herein by reference.

TECHNICAL FIELD

The present disclosure is directed to segmentation of internal structures in images using a multi-stage deep convolutional network that includes a reverse connected first stage.

SUMMARY

According to one innovative aspect of the present disclosure, a method for segmenting internal structures of an internal image is disclosed. In one aspect, the method can include actions of receiving, by a data processing apparatus, data representing image data that depicts internal structures of a subject, providing, by the data processing apparatus, an input data structure to a machine learning model, wherein the input data structure comprises fields structuring data that represents the received data representing the image data that depicts internal structures of the subject, wherein the machine learning model is a multi-stage deep convolutional network that has been trained to segment internal structures depicted by one or more images, receiving, by the data processing apparatus, output data generated by the machine learning model based on the machine learning model's processing of the input data structure, and processing, by the data processing apparatus, the output data to generate rendering data that, when rendered, by one or more computers, causes the one or more computers to output, for display, data that visually distinguishes between different internal structures depicted by the image data.

Other versions include corresponding systems, apparatus, and computer programs to perform the actions of methods defined by instructions encoded on computer readable storage devices.

These and other versions may optionally include one or more of the following features. For instance, in some implementations, the multi-stage deep convolutional network can include a first stage and a second stage.

In some implementations, the first stage of the machine learning model can be configured to: receive the input data structure and generate a first probability map that includes a probability, for each pixel of the image data, that the pixel corresponds to a particular target organ, generate an organ-attention map based on the first probability map and one or more convolutional filters, and generate a second input data structure for input to the second stage, wherein the second input data structure is generated based on the organ-attention map and the image data structured by the fields of the input data structure.

In some implementations, the first stage of the two-stage deep convolutional network can include multiple convolutional layers, wherein each subsequent convolutional layer includes a reverse connection to a prior convolutional layer to feed coarse-scale layer information from the subsequent convolutional layer to the prior fine-scale convolutional layer.

In some implementations, the second stage can be configured to: receive the generated second input data structure, and generate, based on the processing of the generated second input data structure, an adjusted probability map that includes a probability, for each pixel of the image data, that the pixel corresponds to a particular target organ.

In some implementations, the image that depicts internal structures of the object can include a 2D slice of an image from at least one of an axial direction, sagittal direction, or a coronal direction.

In some implementations, the internal structures can include multiple organs of the subject.

In some implementations, the internal structures can include an aorta, a duodenum, an IVC, a liver, one or more kidneys, a pancreas, a spleen, or a stomach.

According to another innovative aspect of the present disclosure, a run-time method for using a trained multi-stage machine learning model for performing multi-organ segmentation of an image depicting internal structures is disclosed. In one aspect, the run-time method can include actions of methods that include obtaining an internal image of an abdomen of a subject, providing the obtained internal image as an input to a first stage of machine learning model that is trained to generate a first probability map that includes, for each pixel, data indicating a likelihood that the pixel corresponds to a particular internal structure based on processing of the obtained internal image, obtaining the first probability map generated by the first stage of the machine learning model, generating input data for a second stage of a machine learning model based on (i) the obtained internal image and (ii) the obtained first probability map, obtaining the generated input data, providing the generated input data as an input to the second stage of the machine learning model that is trained to generate a second probability map that includes, for each pixel, data indicating a likelihood that the pixel corresponds to a particular internal structure based on the processing of the generated input data, obtaining the second probability map generated by the second stage of the machine learning model, and generating based on the second probability map generated by the second machine learning model, output image data, the output image data, when rendered by a user device, causes the user device to display a graphical representation of the obtained internal image that visually distinguishes between different internal structures in the internal image.

Other versions include corresponding systems, apparatus, and computer programs to perform the actions of methods defined by instructions encoded on computer readable storage devices.

According to another innovative aspect of the present disclosure, a method for training a multi-stage machine learning model to perform multi-organ segmentation of an image depicting internal structures is disclosed. In one aspect, training method can include actions of obtaining an training image of an abdomen of a subject, providing the obtained training image as an input to a first stage of machine learning model that is trained to generate a first probability map that includes, for each pixel, data indicating a likelihood that the pixel corresponds to a particular internal structure based on processing of the obtained training image, obtaining the first probability map generated by the first stage of the machine learning model, determining a difference between (i) the first probability map and (ii) a ground truth image having an internal structure label for each pixel of the ground truth image, adjusting one or more parameters of the first stage of the machine learning model based on the difference between (i) the first probability map and (ii) the ground truth image, generating input data for a second stage of a machine learning model based on (i) the obtained training image and (ii) the obtained first probability map, obtaining the generated input data, providing the generated input data as an input to the second stage of the machine learning model that is trained to generate a second probability map that includes, for each pixel, data indicating a likelihood that the pixel corresponds to a particular internal structure based on the processing of the generated input data, obtaining the second probability map generated by the second stage of the machine learning model, determining a difference between (i) the second probability map and (ii) the ground truth image having an internal structure label for each pixel of the ground truth image, and adjusting one or more parameters of the first stage of the machine learning model based on the difference between (i) the second probability map and (ii) the ground truth image.

Other versions include corresponding systems, apparatus, and computer programs to perform the actions of methods defined by instructions encoded on computer readable storage devices.

In accordance with another aspect of the present disclosure, a run-time method for using a plurality of trained multi-stage machine learning models for performing multi-organ segmentation of an image depicting internal structures is disclosed. In one aspect, the method can include obtaining a three-dimensional image depicting internal structures, generating one or more two-dimensional cross-sectional images from the obtained three-dimensional image, providing, each of the one or more two-dimensional cross-sectional images to a respective multi-stage machine learning model that has been trained to generate a second probability map based on processing of an input two-dimensional image, obtaining each second probability map generated by each of the multi-stage machine learning models, and generating a fused image based on the plurality of second probability maps obtained, wherein the fused image is an image that visually distinguishes each internal structure of the internal structures depicted by the obtained three-dimensional image.

Other versions include corresponding systems, apparatus, and computer programs to perform the actions of methods defined by instructions encoded on computer readable storage devices.

These and other aspects of the present disclosure are discussed in more detail in the detailed description below with reference to the accompanying drawings.

BRIEF DESCRIPTION OF THE DRAWINGS

FIG. 2 is a flowchart of an example of a run-time process for using a trained multi-stage machine learning model for performing multi-organ segmentation of CT images.

DETAILED DESCRIPTION

The present disclosure relates to a method, system, machine learning model, and computer program, for a multi-stage machine learning model that can be used to perform multi-organ segmentation of images such as CT images. Multi-stage machine learning model is configured to receive an internal image depicting an image of an abdomen of a living organism such as a human. The multi-stage machine learning model can process input data that includes the received internal image and generate, based on processing of the internal image, output data that annotates each pixel of the received input image with a label that indicates an organ to which the pixel likely corresponds.

Figure 1:
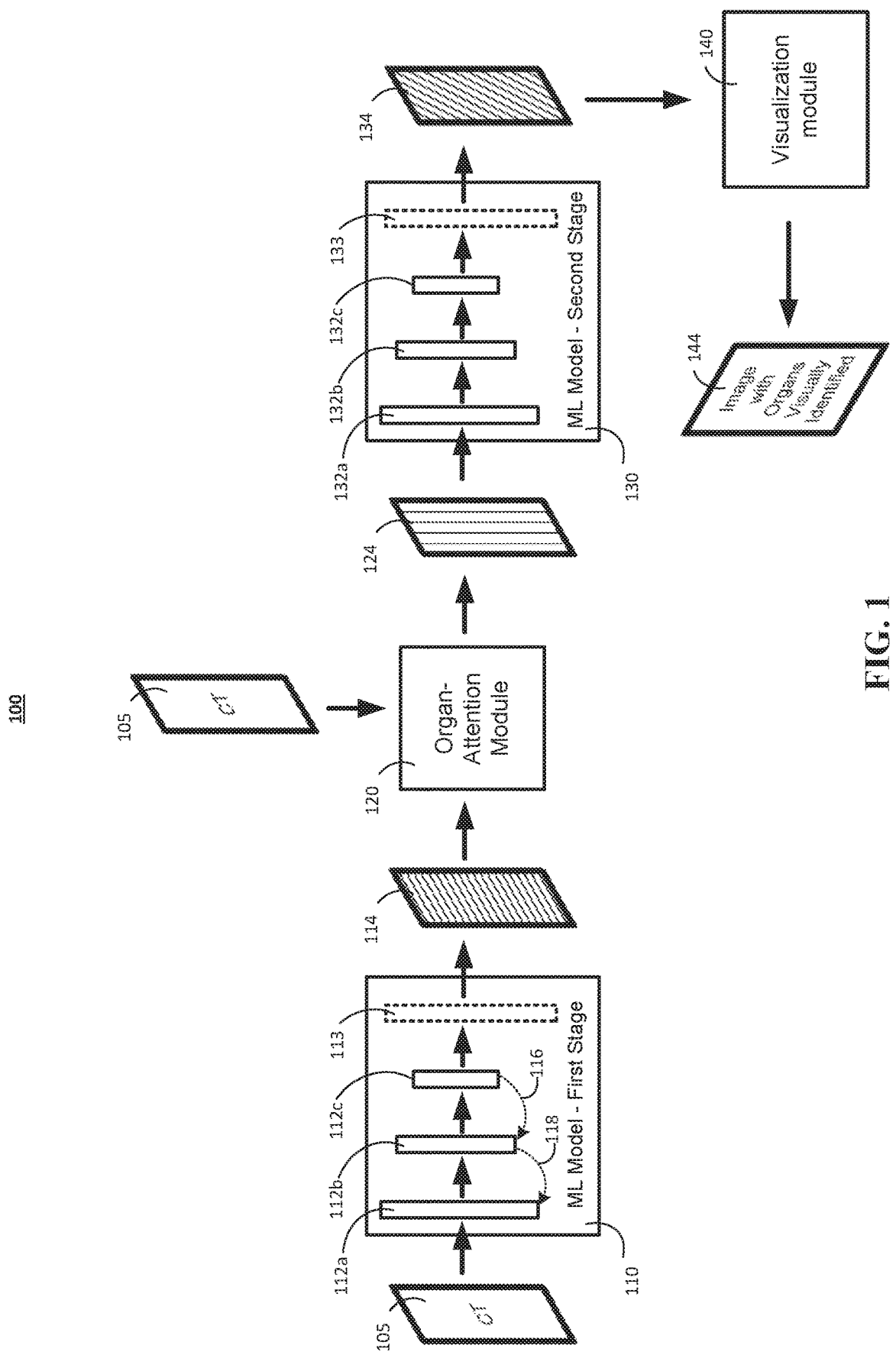
FIG. 1 is a block diagram of an example of a run-time system that uses a trained multi-stage machine learning model for performing multi-organ segmentation of CT images.

FIG. 1 is a block diagram of an example of a run-time system 100 that uses a trained multi-stage machine learning model for performing multi-organ segmentation of CT images. For purposes of this disclosure, multi-organ segmentation of CT images can include segmentation of any internal structure depicted by a CT image and not only organs. Such internal structures can include, for example, an aorta, a duodenum, an inferior vena cava (IVC), a liver, one or more kidneys, a pancreas, a spleen, a stomach, or any other internal structure depicted by an internal image such as a CT image. The system 100 can include a first stage of the machine learning model 110, an organ attenuation module 120, and a second stage of the machine learning model 130. In some implementations, the first stage of the machine learning model 110 and the second stage of the machine learning model can be part of the same machine learning model. In other implementations, the first stage of the machine learning model 110 and the second stage of the machine learning model each be part of separate machine learning models. In some implementations, the machine learning model(s) can include one or more neural networks. The first stage and the second stage of machine learning model 110, 130 can be trained using the system and process described by FIGS. 3 and 4.

The first stage of the machine learning 110 can be trained receive and process input data representing an internal image of an abdomen of a subject such as a human. In some implementations, the internal image 105 can include a CT image. The internal image can depict one or more internal structures of the subject. Internal structures can include, for example, an aorta, a duodenum, an inferior vena cava (IVC), a liver, one or more kidneys, a pancreas, a spleen, a stomach, or any other internal structure depicted by an internal image such as a CT image. In some implementations, the internal image 105 can include a two-dimensional slice of a three-dimensional image from one of the axial, sagittal, and coronal directions. In some implementations, the internal image 105 can be a representation of the internal image 105 such as a vector representation of the internal image 105.

In some implementations, the first stage of the machine learning model 110 can include one or more deep neural networks having one or more convolutional layers. Each convolutional layer can be trained to assign a probability to one or more features of an image processed by the convolutional layer and distinguish the feature from other features of the internal image. For example, a convolutional layer can be configured to identify pixel(s) corresponding to a first internal structure such as a first organ and distinguish the identified pixel(s) from other internal structures such as other organs. In some implementations, for example, the convolutional layer can also assign a probability to a feature such as a pixel or group of pixels indicating a likelihood that the pixel or set of pixels corresponds to a particular internal structure. The example of a first stage of a machine learning model 110 shown in FIG. 1 depicts three convolutional layers 112a, 112b, 112c. However, the present disclosure need not be so limited and the second stage of the machine learning model can include less convolutional layers or more convolutional layers than those depicted in FIG. 1. For example, in some implementations, the first stage of the machine learning model 110 can include many convolutional layers that each correspond to particular pixels, regions of pixels, pixels corresponding to a particular internal structure, or other features of an internal image 105.

The first stage of the machine learning model 110 can process the internal image through each of the convolutional layers 112a, 112b, 112c of the strained first stage 110. In some implementations, the final layer 113 of the first stage of the machine learning model 110 can be used to receive a set of activations from the last convolutional layer 112c and generate a first probability map 114 based on the set of received activations from the final convolutional layer 112c. The first probability map can include, for example, one or more numerical values, for each pixel of the internal image, that each indicate a likelihood that the pixel corresponds to a particular internal structure. In some implementations, each pixel may have up to 1 values, with 1 being the number of target internal structures. Though the example system 100 of FIG. 1 is described as including a first stage of the machine learning model 110 that has a final layer 113 that generates the probability map 114, the present disclosure need not be so limited. Instead, in some implementations, the layer 113 can be separate computing module that is separate from first stage of the machine learning model 110.

In some implementations, the probability map output by the first machine learning model 110 can include a probability map $P^{(1)}=f(I; \Theta^{(1)}) \subset R^{H \times W \times |L|}$ for each label at every pixel, where the probability density function $f(\bullet; \square(1)\Theta^{(1)})$ is a segmentation network parameterized by $\Theta^{(1)}$. Each element $p_{(i,l)}^{(1)} \in P^{(1)}$ is the probability that the ith pixel in the input internal image 105 that belongs to label l, where l=0 is the background and l=1, . . . , |L| are target internal structures. We define $$p_{(i,l)}^{(1)} = \sigma(a_{(i,l)}^{(1)}) = \frac{\exp(a_{(i,l)}^{(1)})}{\sum_{t=0}^{|L|} \exp(a_{(i,t)}^{(1)})} |L|,$$

where $a_{(i,l)}^{(1)}$ is the activation value of the ith pixel on the lth channel dimension. Let $A^{(1)}=\{a_{(i,l)}^{(1)}\}_{i=1, \ldots, H \times W, l=0, \ldots, |L|}$ be the activation map. The objective function to minimize for $\Theta^{(1)}$ is given by $$J^{(1)}(\Theta^{(1)}) = \frac{1}{H \times W} \left[ \sum_{i=1}^{H \times W} \sum_{l=0}^{|L|} 1(t_i = l) \log p_{(i,l)}^{(1)} \right], \quad (1)$$

where l(•) is an indicator function.

The first stage 110 of multi-stage machine learning model can thus perform a preliminary a segmentation of the internal image 105. The initial probability map 114 generated by the layer 113 can be used to generate second input data 124, to the second stage 130, that provides spatial attention to the internal structure locations in the internal image 105 to the second stage 130 of the multi-stage machine learning model. This enables the second stage 130 of the multi-stage machine learning model to be more discriminative for segmenting internal structures and the second stage 130 can primarily deal with local context of image data input into the second stage 130 for processing. This leads to improved results over conventional methods. This multi-stage machine learning model can be referred to as an organ-attention model.

In some implementations, one or more convolutional layers of the first stage of the machine learning model 110 can have a reverse connection 116, 118 to a previous, or lower level, convolutional layer. For example, the convolutional layer 112c can have a reverse connection 116 to the previous convolutional layer 112b. By way of another example, the convolutional layer 112b can have a reverse connection 118 to the previous convolutional layer 112a. These reverse connections 116, 118 enable learned parameters of abstract high-level semantic information to be passed back to the more detailed lower layers so that target internal structures have similar levels of details and abstract information in the same convolutional layer. Those these reverse connections 116, 118 are only shown in the first stage 110. However, other convolutional layers of other stages such as the convolutional layers 132a, 132b, 132c may also have similar types of reverse connections. Such reverse connections are described in more detail in "Abdominal Multi-organ Segmentation with Organ-Attention Networks and Statistical Fusion," to Alan L. Yuille, et al., published Apr. 23, 2018, which is hereby incorporated by reference in its entirety.

The first output data, which is the first probability map 114, generated by the first stage 113 can be provided to an organ-attention module 120. The organ-attention module 120 can be used to generate a second input data 124 for input to the second stage of the machine learning model. In some implementations, the organ-attention module 120 can generate second input data 124 as a function of the original internal image 105 and the first probability map. For example, in some implementations, organ-attention module 120 can generate the second input data to the second stage 130 by using an element-wise product operation to multiply the first probability map 114 by the original representation of the internal image 105 that was input into the first stage 110. This original representation of the internal image 105 may include, for example, a vector representation of the internal image 105. Though referred to as an organ-attention module 120, the images processed by the organ-attention module can also depict any internal structure including, for example, an aorta, a duodenum, an inferior vena cava (IVC), a liver, one or more kidneys, a pancreas, a spleen, a stomach, or the like.

For purposes of this specification, the term module can include one or more software components, one or more hardware components, or any combination thereof, that can be used to realize the functionality attributed to a respective module by this specification. A software component can include, for example, one or more software instructions that, when executed, cause a computer to realize the functionality attributed to a respective module by this specification. A hardware component can include, for example, one or more processors such as a central processing unit (CPU) or graphical processing unit (CPU) that is configured to execute the software instructions to cause the one or more processors to realize the functionality attributed to a module by this specification, a memory device configured to store the software instructions, or a combination thereof. Alternatively, a hardware component can include one or more circuits such as a field programmable gate array (FPGA), an application specific integrated circuit (ASIC), or the like, that has been configured to perform operations using hard-wired logic to realize the functionality attributed to a module by this specification.

The second stage of the machine learning model 130 is trained to be more discriminative for segmenting internal structures such as organs. The second stage 130 is configured to receive, an input, the second input data 124 that is generated by the organ-attention module 120. The second input data 140 is a combination of the original internal image 105 and the first probability map 114.

The second stage 140 can include a deep neural network that includes a plurality of convolutional layers 132a, 132b, 132c. In some implementations, the second stage of the machine learning model 140 can include one or more deep neural networks having one or more convolutional layers. Each convolutional layer can be trained to assign a probability to one or more features of an image processed by the convolutional layer and distinguish the feature from other features of the internal image. For example, a convolutional layer can be configured to identify pixel(s) corresponding to a first internal structure such as an aorta and distinguish the identified pixel(s) from other internal structures such as one or more organs. In some implementations, for example, the convolutional layer can also assign a probability to a feature such as a pixel or group of pixels indicating a likelihood that the pixel or set of pixels corresponds to a particular internal structure. The example of a second stage of a machine learning model 130 shown in FIG. 1 depicts three convolutional layers 113a, 132b, 132c. However, the present disclosure need not be so limited and the second stage of the machine learning model can include less convolutional layers or more convolutional layers than those depicted in FIG. 1. For example, in some implementations, the second stage of the machine learning model 130 can include many convolutional layers that each correspond to particular pixels, regions of pixels, pixels corresponding to a particular internal structure, or other features of the internal image 105.

The second stage of the machine learning model 130 can process the second input data 124 through each of the convolutional layers 132a, 132b, 132c of the trained second stage 130. In some implementations, the final layer 133 of the first stage of the machine learning model 130 can be used to receive a set of activations from the last convolutional layer 112c and generate a second probability map 140 based on the set of received activations from the final convolutional layer 132c. The second probability map can include, for example, one or more numerical values, for each pixel of the internal image, that each indicate a likelihood that the pixel corresponds to a particular internal structure. In some implementations, each pixel may have up to l values, with l being the number of target internal structures. The second probability map 134 can be generated in the same manner as described with respect to the first probability map 114 above. However, this second stage 130 generates second probability map that is more focused on the segmentation between internal structures as a result of the second input data that is generated and provided as an input to the second stage 130. Though the example system 100 of FIG. 1 is described as including a second stage of the machine learning model 130 that has a final layer 133 that generates the second probability map 134, the present disclosure need not be so limited. Instead, in some implementations, the layer 133 can be separate computing module that is separate from second stage of the machine learning model 130. The system 100 can provide the second probability map 134 to the visualization module 140.

The visualization module 140 can be configured to receive the second probability map 134 and generate an output image 144. The output image 144 can be an image, when output on the display of a user device, displays each internal structure in the image 144 in a manner that visually distinguishes each respective internal structure from one another. In some implementations, the internal structures may be visually distinguished using different colors, different shades of colors, different fill patterns (e.g., dotted, diagonal, horizontal lines, vertical lines), or the like. The visualization module 140 can generate the visually distinguished internal structures based on the probabilities and labels in the second probability map 134. In some implementations, the output image 144 may be rendering data that, when rendered by a user device, causes the user device to display an image of the internal structures depicted by internal image 105 such that the internal structures depicted by internal image 105 are visually distinguishable from each respective internal structure.

FIG. 2 is a flowchart of an example of a run-time process 200 or using a trained multi-stage machine learning model for performing multi-organ segmentation of CT images. In general, the process 200 can include obtaining an internal image of an abdomen of a subject (210), providing the obtained internal image as an input to a first stage of machine learning model that is trained to generate a first probability map that includes, for each pixel, data indicating a likelihood that the pixel corresponds to a particular internal structure based on processing of the obtained internal image (220), generating input data for a second stage of a machine learning model based on (i) the obtained internal image and (ii) the first probability map (230), providing the generated input data as an input to the second stage of the machine learning model that is trained to generate a second probability map that includes, for each pixel, data indicating a likelihood that the pixel corresponds to a particular internal structure based on the processing of the input generated at stage 230 (240), and generating based on the second probability map generated by the second machine learning model, output image data, the output image data, when rendered by a user device, causes the user device to display a graphical representation of the obtained internal image that visually distinguishes between different internal structures in the internal image 250.

Figure 3:
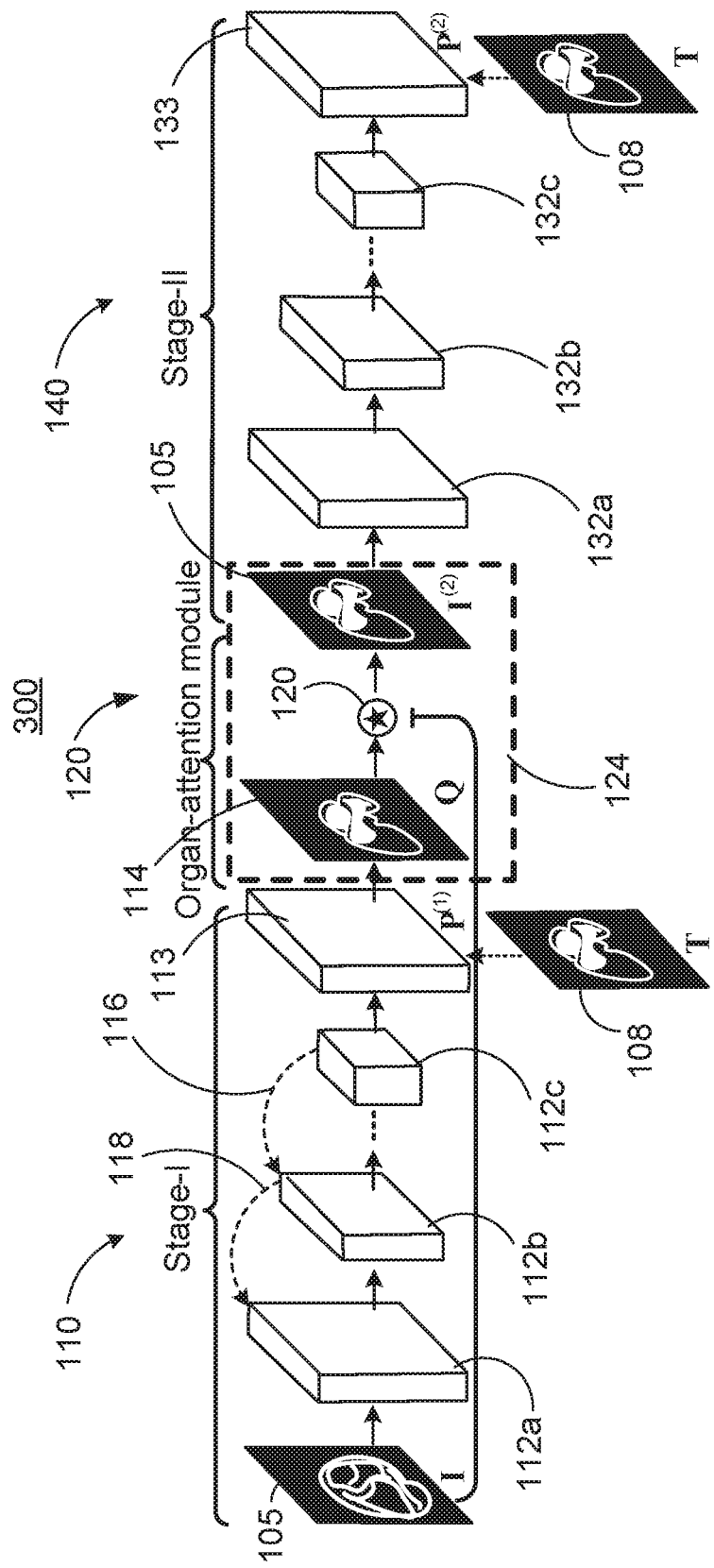
FIG. 3 is a diagram of an example of a system for training a multi-stage machine learning model to perform multi-organ segmentation of CT images.

FIG. 3 is a diagram of an example of a system 300 for training a multi-stage machine learning model to perform multi-organ segmentation of CT images. The system 300 can include an input image 105, a first stage 110 of a machine learning model that includes one or more convolutional layers 112a, 112b, 112c, a module 113 for generate a first probability map 114, an organ-attention module 120 that operates on the first probability map 114 and the input image 105, a second stage 130 of the machine learning model that includes one or more convolutional layers 132a, 132b, 132c, and a module 114 for generate a second probability map 133. Elements of FIG. 3 that share like numbers to a corresponding portion of FIG. 1 represent the same element as shown in FIG. 1, but during training.

The system 300 can begin training a multi-stage machine learning model to perform the operations described with reference to FIGS. 1 and 2 by obtaining an input image 105. The obtained image can include an image that depicts internal structures in an abdomen of a subject such as human. In some implementations, the obtained image can be an actual CT image obtained from a library of training images. In other implementations, the obtained image can include a CT image that was generated by a simulator for training the multi-stage machine learning model. In yet other implementations, the image can be a different type of image shown internal structures of an abdomen such as an MRI image, an X-Ray image, an Ultrasound image, or the like.

The system 300 can process the obtained image 105 through each of the convolutional layers 112a, 112b, 112c. The set of activation data output by the last convolutional layer 112c can be provided as an input to the module 113. The module 113 can process the set of activation data and generate a first probability map as described above with reference to FIG. 1. In some implementations, the module 113 may be a final layer of the first stage 110. In other implementations, the module 113 may be a separate stand along module that is a different computing module than the first stage 110.

The system 300 can obtain the first probability map 114 generated by the module 113 and compare the first probability map to a labeled input image 108. The labeled input image can include the image 105 that has had each pixel labeled as corresponding to a particular internal structure. The system 300 can determine the difference between the first probability map 114 generated by the module 113 and the image 108 using a loss function. Then, the system 300, can update the parameters of one or more of the convolutional layers 112a, 112b, 112c of the first stage 110 based on the difference between the first probability map 114 produced by the module 113 and the labeled input image 108, which represents the ground truth. The system 300 can iteratively update the parameters of the one or more convolutional layers 112a, 112b, 112c for different training inputs until the loss function is optimized. An example loss function is described later below.

The system 300 can continue training the multi-stage machine learning model by using the organ-attention module to generate second input data for input to the second stage of the multi-stage machine learning model 130. In some implementations, for example, the organ-attention module 120 can generate second input data 124 as a function of the original internal image 105 and the first probability map 114. In some implementations, for example, the organ-attention module 120 can generate the second input data to the second stage 130 by using an element-wise product operation to multiply the first probability map 114 by the original representation of the internal image 105 that was input into the first stage 110. In this example, the result of the multiplication can serve as the input 124 to the second stage 140. This original representation of the internal image 105 may include, for example, a vector representation of the internal image 105.

The system 300 can process the generated second input data through each of the convolutional layers 132a, 132b, 132c. The set of activation data output by the last convolutional layer 132c can be provided as an input to the module 133. The module 133 can process the set of activation data and generate a second probability map as described above with reference to FIG. 1. In some implementations, the module 133 may be a final layer of the second stage 140. In other implementations, the module 133 may be a separate stand along module that is a different computing module than the second stage 140.

The system 300 can obtain the second probability map generated by the module 113 (not explicitly shown in FIG. 3) and compare the second probability map to a labeled input image 108. The labeled input image can include the image 105 that has had each pixel labeled as corresponding to a particular internal structure. The system 300 can determine the difference between the second probability map generated by the module 133 and the image 108 using a loss function. Then, the system 300, can update the parameters of one or more of the convolutional layers 132a, 132b, 132c of the second stage 140 based on the difference between the second probability map by the module 133 and the labeled input image 108, which represents the ground truth. The system 300 can iteratively update the parameters of the one or more convolutional layers 132a, 132b, 132c for different training inputs until the loss function is optimized. An example loss function is described later below.

In one implementation, to jointly optimize first stage 110 and stage 140, a loss function that estimates parameters aiming at estimating parameters $\Theta^{(1)}$ for the first probability map and $\Theta^{(2)}$ for the second probability map, W, and b by optimizing the function:

$$J = h^{(1)} J^{(1)}(\Theta^{(1)}) + h^{(2)} J^{(2)}(\Theta^{(2)}, W, b),$$

where, W indicates convolutional filters, for example, whose dimension is (5×5|L|), b is bias, $\Theta^{(1)}$ includes one or more performance parameters of the first stage of the machine learning model, $\Theta^{(2)}$ one or more performance parameters of the second stage of the machine learning model, $h^1$ and $h^2$ are fusion weights, and J is the total loss function that is the weighted average of loss functions $J^1$ for the first stage of the machine learning mode and $J^2$ for the second stage of the machine learning model. $J^1$ is dependent on $\Theta^{(1)}$ and $J^2$ is dependent on $\Theta^{(2)}$. In some implementations, using a stronger fusion weight, $h^2$, for the second stage of the machine learning model than the fusion weight, $h^1$, for the first stage of the machine learning model such that $h^1 < h^2$ can result in better performance relative to implementations where $h^1 \geq h^2$. In at least one implementation, values of $h^1 = 0.5$ and $h^2 = 1.5$ can be set and fixed at these values during training.

Figure 4:
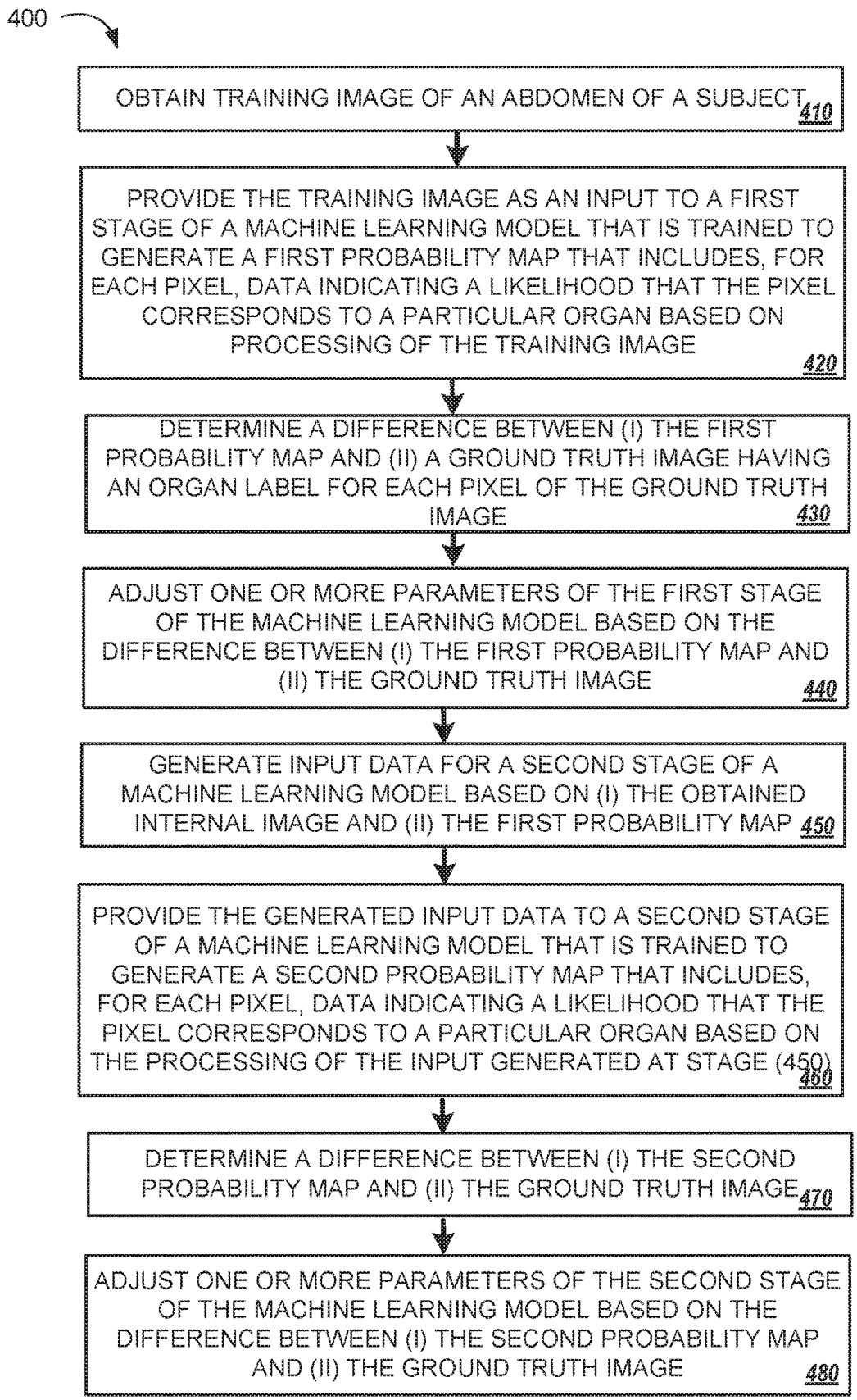
FIG. 4 is a flowchart of an example of a process for training a multi-stage machine learning model to perform multi-organ segmentation of CT images.

FIG. 4 is a flowchart of an example of a process 400 for training a multi-stage machine learning model to perform multi-organ segmentation of CT images. In general, the process 400 can include obtaining an training image of an abdomen of a subject (410), providing the obtained training image as an input to a first stage of machine learning model that is trained to generate a first probability map that includes, for each pixel, data indicating a likelihood that the pixel corresponds to a particular internal structure based on processing of the obtained training image (420), determining a difference between (i) the first probability map and (ii) a ground truth image having an internal structure label for each pixel of the ground truth image (430), adjusting one or more parameters of the first stage of the machine learning model based on the difference between (i) the first probability map and (ii) the ground truth image (440), generating input data for a second stage of a machine learning model based on (i) the obtained training image and (ii) the first probability map (450), providing the generated input data as an input to the second stage of the machine learning model that is trained to generate a second probability map that includes, for each pixel, data indicating a likelihood that the pixel corresponds to a particular internal structure based on the processing of the input generated at stage 450 (460), determining a difference between (i) the second probability map and (ii) the ground truth image having an internal structure label for each pixel of the ground truth image (470), and adjusting one or more parameters of the first stage of the machine learning model based on the difference between (i) the second probability map and (ii) the ground truth image (480).

The process 400 may be iteratively performed for multiple different training images until a loss function that measures the difference between the respective probability maps and the ground truth image is optimized.

Figure 5:
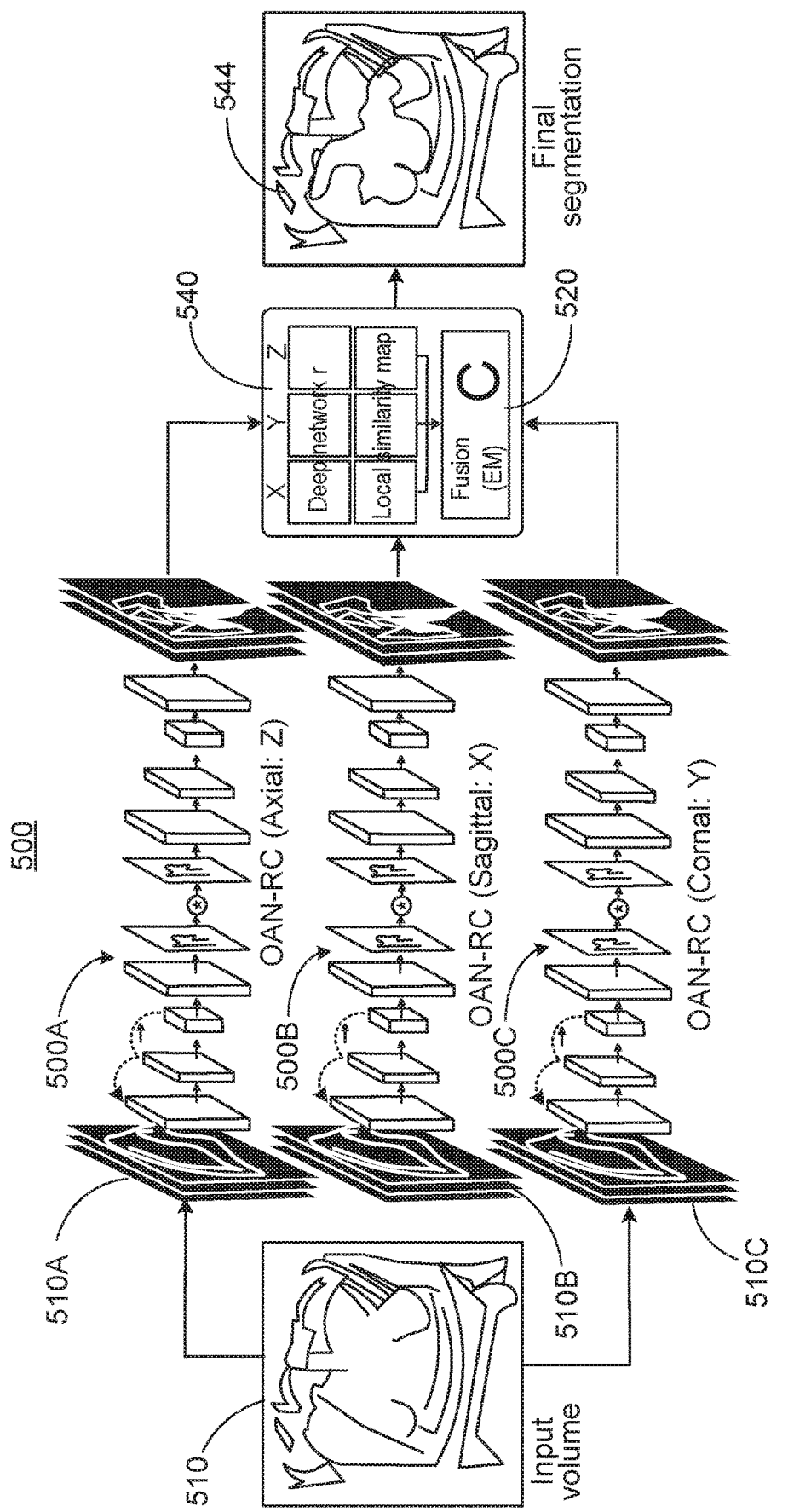
FIG. 5. is a diagram of an example of a system that uses a plurality of trained multi-stage machine learning models to perform multi-organ segmentation of CT images.

FIG. 5. is a diagram of an example of a system 500 that uses a plurality of trained multi-stage machine learning models to perform multi-organ segmentation of CT images. The system 500 can use multiple instances of the system 100 to analyze different cross sections of a CT image of a subject's abdomen.

The system 500 can be configured to receive input image 510 such as a three-dimensional CT image. In some implementations, the system 500 can use a computing module such as an extraction module to obtain multiple different cross-sections of the input image 510. By way of example, the system 500 can obtain an axial image cross-section 510A, a sagittal image cross-section 510B, and a coronal image cross-section 510C. Note that FIG. 5 generally shows the process of dividing an input image 510 into multiple cross-sections 510A, 510B, 510C. However, the actual image use in FIG. 5 may not actually depict cross-section 510A, a sagittal image cross-section 510B, and a coronal image cross-section 510C.

The sub-system 500A is the same system as that set forth with respect to FIG. 1, 100. The system 500 can use the sub-system 500A to process the axial image cross-section 510A and generate first output data, which can be provided as an input to the visualization module 540. The first output generated by the sub-system 500A can include a second probability map, as described with reference to the system 100 of FIG. 1. The sub-system 500A can generate the first output which includes the second probability map in the same manner as the system 100 of FIG. 1 processes the input internal image 105 to generate a second probability map.

Likewise, the sub-system 500B is the same system as that set forth with respect to FIG. 1, 100. The system 500 can use the sub-system 500B to process the sagittal image cross-section 510B and generate second output data, which can be provided as an input to the visualization module 540. The second output generated by the sub-system 500B can include another second probability map, as described with reference to the system 100 of FIG. 1. The sub-system 500B can generate the second output which includes the other second probability map in the same manner as the system 100 of FIG. 1 processes the input internal image 105 to generate a second probability map.

Similarly, the system 500 can use the sub-system 500C to process the coronal image cross-section 510C and generate third output data, which can be provided as an input to the visualization module 540. The third output generated by the sub-system 500C can include another second probability map, as described with reference to the system 100 of FIG. 1. The sub-system 500C can generate the third output which includes other second probability map by processing the coronal cross-section image 510C in the same manner as the system 100 of FIG. 1 processes the input internal image 105 to generate a second probability map. The first output of the sub-system 500A, the second output of sub-system 500B, and the third output of sub-system 500C each include a second probability map, as described with reference to FIGS. 1 and 2.

The system 500 can then use a visualization module 540 use a fusion module 520 to fuse the first output data generated by sub-system 500A based on 500A processing image 510A, the second output data generated by sub-system 500B based on 500B processing image 510B, and the third output data generated by sub-system 500C based on 500C processing image 510C a single output image. The fusion module 520 can generate the single output image based on the output data generated by subsystems 500A, 500B, 500C in a number of different ways by processing input data the fusion module 520 receives. In some implementations, for example, the fusion module 520 can execute Boolean operations such as a union, intersection, or a combination thereof, on the output data generated by the subsystems 500A, 500B, 500C to generate a single probability map. Then, the single probability map can be used to generate the fused image 544 by generating rendering data, that when rendered by a user device, causes the user device to generate an image that visually distinguishes portions of an image corresponding to the image 510 using probabilities of the single probability map, internal structure labels of the single probability map, or a combination thereof, to visually differentiate between internal structures of an image that corresponds to the image 510.

In other implementations, the fusion module 520 can use majority voting as a method for generating the fused image 544 from the multiple sets of output data generated by the subsystems 500A, 500B, 500C. In other implementations, the fusion module 520 can use label fusion algorithms that use an expectation-maximization (EM) framework such as simultaneous truth and performance level estimation (STAPLE). In other implementations, the system 500 can generate local similarity maps associated with each cross-sectional image, the output data generated by a sub-system for each respective cross-sectional image, or a combination thereof, and generate the fused image 520 using the generated local similarity maps. In other implementations, the fusion module 520 can generate a fused image 544 from the output data generated by the subsystems 500A, 500B, 500C using an image fusion process described by "Abdominal Multi-organ Segmentation with Organ-Attention Networks and Statistical Fusion," to Alan L. Yuille, et al., published Apr. 23, 2018, which is hereby incorporated by reference in its entirety.

Figure 6:
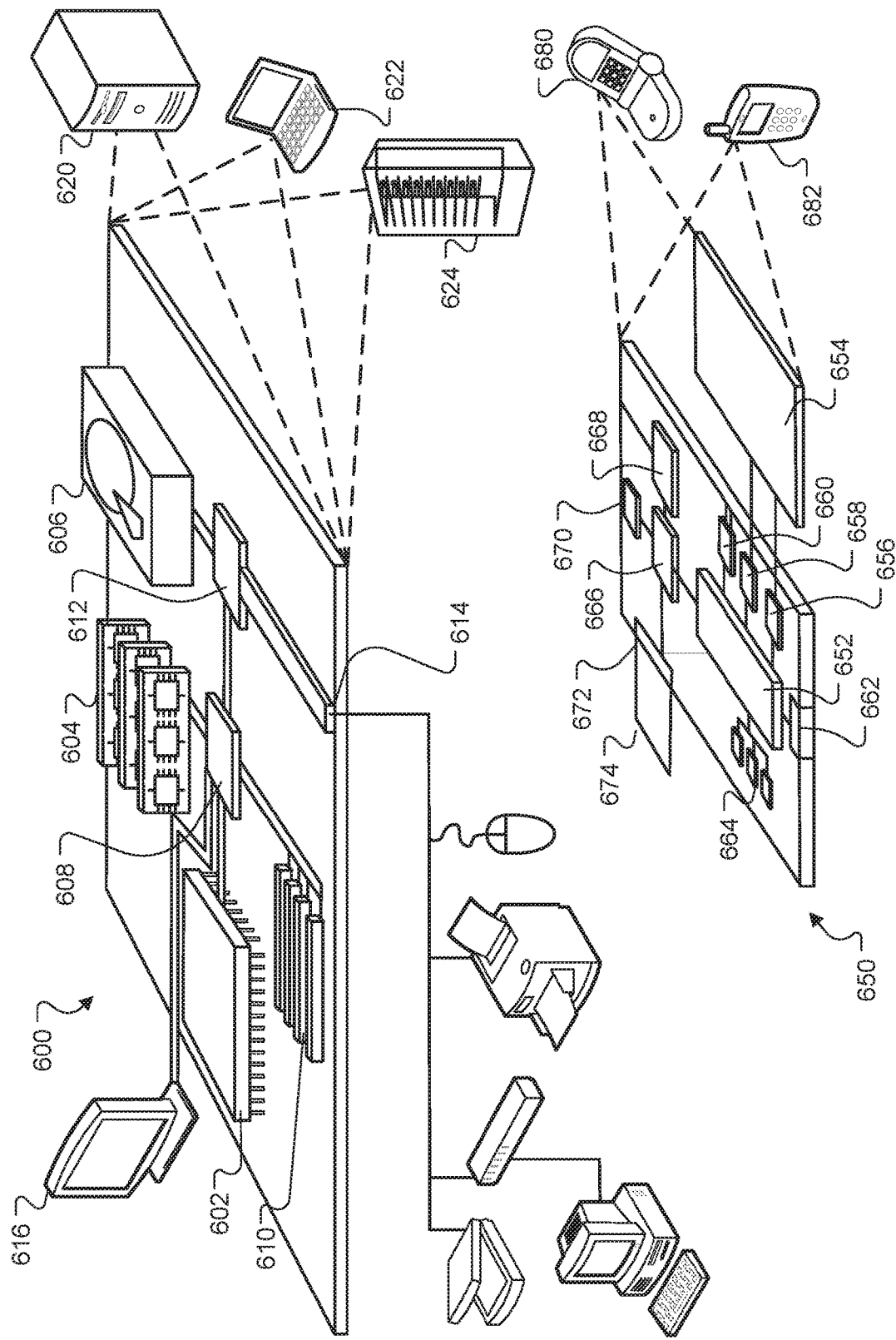
FIG. 6 is a block diagram of an example of system components that can be used to implement the multi-stage learning model for performing multi-organ segmentation of CT images.

FIG. 6 is a block diagram of an example of system components that can be used to implement the multi-stage learning model for performing multi-organ segmentation of CT images.

Computing device 600 is intended to represent various forms of digital computers, such as laptops, desktops, workstations, personal digital assistants, servers, blade servers, mainframes, and other appropriate computers. Computing device 650 is intended to represent various forms of mobile devices, such as personal digital assistants, cellular telephones, smartphones, and other similar computing devices. Additionally, computing device 600 or 650 can include Universal Serial Bus (USB) flash drives. The USB flash drives can store operating systems and other applications. The USB flash drives can include input/output components, such as a wireless transmitter or USB connector that can be inserted into a USB port of another computing device. The components shown here, their connections and relationships, and their functions, are meant to be examples only, and are not meant to limit implementations of the inventions described and/or claimed in this document.

Computing device 600 includes a processor 602, memory 604, a storage device 608, a high-speed interface 608 connecting to memory 604 and high-speed expansion ports 610, and a low speed interface 612 connecting to low speed bus 614 and storage device 608. Each of the components 602, 604, 608, 608, 610, and 612, are interconnected using various busses, and can be mounted on a common motherboard or in other manners as appropriate. The processor 602 can process instructions for execution within the computing device 600, including instructions stored in the memory 604 or on the storage device 608 to display graphical information for a GUI on an external input/output device, such as display 616 coupled to high speed interface 608. In other implementations, multiple processors and/or multiple buses can be used, as appropriate, along with multiple memories and types of memory. Also, multiple computing devices 600 can be connected, with each device providing portions of the necessary operations, e.g., as a server bank, a group of blade servers, or a multi-processor system.

The memory 604 stores information within the computing device 600. In one implementation, the memory 604 is a volatile memory unit or units. In another implementation, the memory 604 is a non-volatile memory unit or units. The memory 604 can also be another form of computer-readable medium, such as a magnetic or optical disk.

The storage device 608 is capable of providing mass storage for the computing device 600. In one implementation, the storage device 608 can be or contain a computer-readable medium, such as a floppy disk device, a hard disk device, an optical disk device, or a tape device, a flash memory or other similar solid-state memory device, or an array of devices, including devices in a storage area network or other configurations. A computer program product can be tangibly embodied in an information carrier. The computer program product can also contain instructions that, when executed, perform one or more methods, such as those described above. The information carrier is a computer- or machine-readable medium, such as the memory 604, the storage device 608, or memory on processor 602.

The high-speed controller 608 manages bandwidth-intensive operations for the computing device 600, while the low speed controller 612 manages lower bandwidth intensive operations. Such allocation of functions is only an example. In one implementation, the high-speed controller 608 is coupled to memory 604, display 616, e.g., through a graphics processor or accelerator, and to high-speed expansion ports 610, which can accept various expansion cards (not shown). In the implementation, low-speed controller 612 is coupled to storage device 608 and low-speed expansion port 614. The low-speed expansion port, which can include various communication ports, e.g., USB, Bluetooth, Ethernet, wireless Ethernet can be coupled to one or more input/output devices, such as a keyboard, a pointing device, microphone/speaker pair, a scanner, or a networking device such as a switch or router, e.g., through a network adapter. The computing device 600 can be implemented in a number of different forms, as shown in the figure. For example, it can be implemented as a standard server 620, or multiple times in a group of such servers. It can also be implemented as part of a rack server system 624. In addition, it can be implemented in a personal computer such as a laptop computer 622. Alternatively, components from computing device 600 can be combined with other components in a mobile device (not shown), such as device 650. Each of such devices can contain one or more of computing device 600, 650, and an entire system can be made up of multiple computing devices 600, 650 communicating with each other.

The computing device 600 can be implemented in a number of different forms, as shown in the figure. For example, it can be implemented as a standard server 620, or multiple times in a group of such servers. It can also be implemented as part of a rack server system 624. In addition, it can be implemented in a personal computer such as a laptop computer 622. Alternatively, components from computing device 600 can be combined with other components in a mobile device (not shown), such as device 650. Each of such devices can contain one or more of computing device 600, 650, and an entire system can be made up of multiple computing devices 600, 650 communicating with each other.

Computing device 650 includes a processor 652, memory 664, and an input/output device such as a display 654, a communication interface 666, and a transceiver 668, among other components. The device 650 can also be provided with a storage device, such as a micro-drive or other device, to provide additional storage. Each of the components 650, 652, 664, 654, 666, and 668, are interconnected using various buses, and several of the components can be mounted on a common motherboard or in other manners as appropriate.

The processor 652 can execute instructions within the computing device 650, including instructions stored in the memory 664. The processor can be implemented as a chipset of chips that include separate and multiple analog and digital processors. Additionally, the processor can be implemented using any of a number of architectures. For example, the processor 610 can be a CISC (Complex Instruction Set Computers) processor, a RISC (Reduced Instruction Set Computer) processor, or a MISC (Minimal Instruction Set Computer) processor. The processor can provide, for example, for coordination of the other components of the device 650, such as control of user interfaces, applications run by device 650, and wireless communication by device 650.

Processor 652 can communicate with a user through control interface 658 and display interface 656 coupled to a display 654. The display 654 can be, for example, a TFT (Thin-Film-Transistor Liquid Crystal Display) display or an OLED (Organic Light Emitting Diode) display, or other appropriate display technology. The display interface 656 can comprise appropriate circuitry for driving the display 654 to present graphical and other information to a user. The control interface 658 can receive commands from a user and convert them for submission to the processor 652. In addition, an external interface 662 can be provided in communication with processor 652, so as to enable near area communication of device 650 with other devices. External interface 662 can provide, for example, for wired communication in some implementations, or for wireless communication in other implementations, and multiple interfaces can also be used.

The memory 664 stores information within the computing device 650. The memory 664 can be implemented as one or more of a computer-readable medium or media, a volatile memory unit or units, or a non-volatile memory unit or units. Expansion memory 674 can also be provided and connected to device 650 through expansion interface 672, which can include, for example, a SIMM (Single In Line Memory Module) card interface. Such expansion memory 674 can provide extra storage space for device 650, or can also store applications or other information for device 650. Specifically, expansion memory 674 can include instructions to carry out or supplement the processes described above, and can also include secure information. Thus, for example, expansion memory 674 can be provided as a security module for device 650, and can be programmed with instructions that permit secure use of device 650. In addition, secure applications can be provided via the SIMM cards, along with additional information, such as placing identifying information on the SIMM card in a non-hackable manner.

The memory can include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 664, expansion memory 674, or memory on processor 652 that can be received, for example, over transceiver 668 or external interface 662.

Device 650 can communicate wirelessly through communication interface 666, which can include digital signal processing circuitry where necessary. Communication interface 666 can provide for communications under various modes or protocols, such as GSM voice calls, SMS, EMS, or MMS messaging, CDMA, TDMA, PDC, WCDMA, CDMA2000, or GPRS, among others. Such communication can occur, for example, through radio-frequency transceiver 668. In addition, short-range communication can occur, such as using a Bluetooth, Wi-Fi, or other such transceiver (not shown). In addition, GPS (Global Positioning System) receiver module 670 can provide additional navigation- and location-related wireless data to device 650, which can be used as appropriate by applications running on device 650.

Device 650 can also communicate audibly using audio codec 660, which can receive spoken information from a user and convert it to usable digital information. Audio codec 660 can likewise generate audible sound for a user, such as through a speaker, e.g., in a handset of device 650. Such sound can include sound from voice telephone calls, can include recorded sound, e.g., voice messages, music files, etc. and can also include sound generated by applications operating on device 650.

The computing device 650 can be implemented in a number of different forms, as shown in the figure. For example, it can be implemented as a cellular telephone 680. It can also be implemented as part of a smartphone 682, personal digital assistant, or other similar mobile device.

Various implementations of the systems and methods described here can be realized in digital electronic circuitry, integrated circuitry, specially designed ASICs (application specific integrated circuits), computer hardware, firmware, software, and/or combinations of such implementations. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor for displaying information to the user and a keyboard and a pointing device, e.g., a mouse or a trackball by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the systems and techniques described here, or any combination of such back end, middleware, or front end components. The components of the system can be interconnected by any form or medium of digital data communication, e.g., a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

Other Embodiments

A number of embodiments have been described. Nevertheless, it will be understood that various modifications can be made without departing from the spirit and scope of the invention. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

The invention claimed is:

1. A data apparatus for segmenting internal structures depicted in an image, the data processing apparatus including one or more processors and one or more computer readable storage media storing instructions, that when executed by the one or more processors, causes the one or more processors to perform operations, the operations comprising:
receiving, by the data processing apparatus, data representing image data that depicts internal structures of a subject;
providing, by the data processing apparatus, an input data structure to a machine learning model, wherein the input data structure comprises fields structuring data that represents the received data representing the image data that depicts internal structures of the subject, wherein the machine learning model is a multi-stage deep convolutional network that has been trained to segment internal structures depicted by one or more images, wherein the multi-stage deep convolutional network includes a first stage and a second stage, wherein the first stage is configured to:
- receive the input data structure and generate a first probability map that includes a probability, for each pixel of the image data, that the pixel corresponds to a particular target organ;
- generate an organ-attention map based on the first probability map and one or more convolutional filters; and
- generate a second input data structure for input to the second stage, wherein the second input data structure is generated based on the organ-attention map and the image data structured by the fields of the input data structure;

processing, by the data processing apparatus, the provided input data structure through the machine learning model;

receiving, by the data processing apparatus, output data generated by the machine learning model based on the machine learning model's processing of the input data structure; and processing, by the data processing apparatus, the output data to generate rendering data that, when rendered, by one or more computers, causes the one or more computers to output, for display, data that visually distinguishes between different internal structures depicted by the image data.

2. The data processing apparatus of claim 1, wherein the first stage of the two-stage deep convolutional network includes multiple convolutional layers, wherein each subsequent convolutional layer includes a reverse connection to a prior convolutional layer to feed coarse-scale layer information from the subsequent convolutional layer to the prior fine-scale convolutional layer.

3. The data processing apparatus of claim 1,
wherein the second stage is configured to:
- receive the generated second input data structure; and
- generate, based on the processing of the generated second input data structure, an adjusted probability map that includes a probability, for each pixel of the image data, that the pixel corresponds to a particular target organ.

4. The data processing apparatus of claim 1, wherein the image that depicts internal structures of the object includes a 2D slice of an image from at least one of an axial direction, sagittal direction, or a coronal direction.

5. The data processing apparatus of claim 1, wherein the internal structures include multiple organs of the subject.

6. The data processing apparatus of claim 1, wherein the internal structures include an aorta, a duodenum, an IVC, a liver, one or more kidneys, a pancreas, a spleen, or a stomach.

7. A method comprising:
receiving, by a data processing apparatus, data representing image data that depicts internal structures of a subject;
providing, by the data processing apparatus, an input data structure to a machine learning model, wherein the input data structure comprises fields structuring data that represents the received data representing the image data that depicts internal structures of the subject, wherein the machine learning model is a multi-stage deep convolutional network that has been trained to segment internal structures depicted by one or more images, wherein the multi-stage deep convolutional network includes a first stage and a second stage, wherein the first stage is configured to:
- receive the input data structure and generate a first probability map that includes a probability, for each pixel of the image data, that the pixel corresponds to a particular target organ;
- generate an organ-attention map based on the first probability map and one or more convolutional filters; and
- generate a second input data structure for input to the second stage, wherein the second input data structure is generated based on the organ-attention map and the image data structured by the fields of the input data structure;

processing, by the data processing apparatus, the provided input data structure through the machine learning model;

receiving, by the data processing apparatus, output data generated by the machine learning model based on the machine learning model's processing of the input data structure; and processing, by the data processing apparatus, the output data to generate rendering data that, when rendered, by one or more computers, causes the one or more computers to output, for display, data that visually distinguishes between different internal structures depicted by the image data.

8. The method of claim 7, wherein the first stage of the two-stage deep convolutional network includes multiple convolutional layers, wherein each subsequent convolutional layer includes a reverse connection to a prior convolutional layer to feed coarse-scale layer information from the subsequent convolutional layer to the prior fine-scale convolutional layer.

9. The method of claim 7,
wherein the second stage is configured to:
- receive the generated second input data structure; and
- generate, based on the processing of the generated second input data structure, an adjusted probability map that includes a probability, for each pixel of the image data, that the pixel corresponds to a particular target organ.

10. The method of claim 7, wherein the image that depicts internal structures of the object includes a 2D slice of an image from at least one of an axial direction, sagittal direction, or a coronal direction.

11. The method of claim 7, wherein the internal structures include multiple organs of the subject.

12. The method of claim 7, wherein the internal structures include an aorta, a duodenum, an IVC, a liver, one or more kidneys, a pancreas, a spleen, or a stomach.

13. A non-transitory computer-readable medium storing software comprising instructions executable by one or more computers which, upon such execution, cause the one or more computers to perform operations, the operations comprising:
receiving, by a data processing apparatus, data representing image data that depicts internal structures of a subject;
providing, by the data processing apparatus, an input data structure to a machine learning model, wherein the input data structure comprises fields structuring data that represents the received data representing the image data that depicts internal structures of the subject, wherein the machine learning model is a multi-stage deep convolutional network that has been trained to segment internal structures depicted by one or more images, wherein the multi-stage deep convolutional network includes a first stage and a second stage, wherein the first stage is configured to:
  receive the input data structure and generate a first probability map that includes a probability, for each pixel of the image data, that the pixel corresponds to a particular target organ;
  generate an organ-attention map based on the first probability map and one or more convolutional filters; and
  generate a second input data structure for input to the second stage, wherein the second input data structure is generated based on the organ-attention map and the image data structured by the fields of the input data structure;
processing, by the data processing apparatus, the provided input data structure through the machine learning model;
receiving, by the data processing apparatus, output data generated by the machine learning model based on the machine learning model's processing of the input data structure; and
processing, by the data processing apparatus, the output data to generate rendering data that, when rendered, by one or more computers, causes the one or more computers to output, for display, data that visually distinguishes between different internal structures depicted by the image data.

14. The non-transitory computer-readable medium of claim 13,
  wherein the second stage is configured to:
    receive the generated second input data structure; and
    generate, based on the processing of the generated second input data structure, an adjusted probability map that includes a probability, for each pixel of the image data, that the pixel corresponds to a particular target organ.

15. The non-transitory computer-readable medium of claim 13, wherein the first stage of the two-stage deep convolutional network includes multiple convolutional layers, wherein each subsequent convolutional layer includes a reverse connection to a prior convolutional layer to feed coarse-scale layer information from the subsequent convolutional layer to the prior fine-scale convolutional layer.

16. The non-transitory computer-readable medium of claim 13, wherein the image that depicts internal structures of the object includes a 2D slice of an image from at least one of an axial direction, sagittal direction, or a coronal direction.

17. The non-transitory computer-readable medium of claim 13, wherein the internal structures include multiple organs of the subject.

18. The non-transitory computer-readable medium of claim 13, wherein the internal structures include an aorta, a duodenum, an IVC, a liver, one or more kidneys, a pancreas, a spleen, or a stomach.

* * * * *